United States Patent
Quayle et al.

(10) Patent No.: US 9,949,972 B2
(45) Date of Patent: Apr. 24, 2018

(54) COMBINATIONS OF HISTONE DEACETYLASE INHIBITORS AND IMMUNOMODULATORY DRUGS

(71) Applicant: Acetylon Pharmaceuticals, Inc., Boston, MA (US)

(72) Inventors: Steven Norman Quayle, Brookline, MA (US); Simon Stewart Jones, Harvard, MA (US)

(73) Assignee: ACETYLON PHARMACEUTICALS, INC, Boston, MA (US)

( * ) Notice: Subject to any disclaimer, the term of this patent is extended or adjusted under 35 U.S.C. 154(b) by 22 days.

(21) Appl. No.: 14/558,941

(22) Filed: Dec. 3, 2014

(65) Prior Publication Data

US 2015/0150871 A1    Jun. 4, 2015

Related U.S. Application Data

(60) Provisional application No. 61/911,086, filed on Dec. 3, 2013, provisional application No. 62/061,368, filed on Oct. 8, 2014.

(51) Int. Cl.
| | | |
|---|---|---|
| *A61K 31/505* | (2006.01) | |
| *A61K 31/4439* | (2006.01) | |
| *A61K 31/454* | (2006.01) | |
| *A61K 45/06* | (2006.01) | |

(52) U.S. Cl.
CPC ........ *A61K 31/505* (2013.01); *A61K 31/4439* (2013.01); *A61K 31/454* (2013.01); *A61K 45/06* (2013.01)

(58) Field of Classification Search
None
See application file for complete search history.

(56) References Cited

U.S. PATENT DOCUMENTS

| | | |
|---|---|---|
| 3,549,633 A | 12/1970 | Grabowski et al. |
| 5,635,517 A | 6/1997 | Muller et al. |
| 6,281,230 B1 | 8/2001 | Muller et al. |
| 6,335,349 B1 | 1/2002 | Muller et al. |
| 6,476,052 B1 | 11/2002 | Muller et al. |
| 6,777,217 B1 | 8/2004 | Schreiber et al. |
| 7,244,853 B2 | 7/2007 | Schreiber et al. |
| 7,250,504 B2 | 7/2007 | Grozinger et al. |
| 7,994,362 B2 | 8/2011 | Schreiber et al. |
| 8,148,526 B1 | 4/2012 | van Duzer et al. |
| 8,394,810 B2 | 3/2013 | van Duzer et al. |
| 8,609,678 B2 | 12/2013 | van Duzer et al. |
| 8,614,223 B2 | 12/2013 | van Duzer et al. |
| 8,999,289 B2 | 4/2015 | Anderson et al. |
| 9,096,549 B2 | 8/2015 | van Duzer et al. |
| 9,139,583 B2 | 9/2015 | van Duzer et al. |
| 9,145,412 B2 | 9/2015 | van Duzer et al. |
| 9,278,963 B2 | 3/2016 | van Duzer et al. |
| 2004/0266769 A1 | 12/2004 | Bressi et al. |
| 2005/0119305 A1 | 6/2005 | Naka et al. |
| 2006/0239909 A1 | 10/2006 | Anderson et al. |
| 2007/0093413 A1 | 4/2007 | Schreiber et al. |
| 2007/0149495 A1 | 6/2007 | Bressi et al. |
| 2008/0207590 A1 | 8/2008 | Deziel et al. |
| 2008/0317708 A1 | 12/2008 | Zeldis |
| 2009/0023786 A1 | 1/2009 | Miller et al. |
| 2009/0209590 A1 | 8/2009 | Mazitschek et al. |
| 2009/0227674 A1 | 9/2009 | Richon et al. |
| 2009/0305384 A1 | 12/2009 | Grozinger et al. |
| 2009/0312363 A1 | 12/2009 | Bradner et al. |
| 2010/0098657 A1 | 4/2010 | Schafer et al. |
| 2010/0137196 A1 | 6/2010 | Schreiber et al. |
| 2010/0152254 A1 | 6/2010 | Bialer et al. |
| 2010/0168463 A1 | 7/2010 | Hirata et al. |
| 2010/0330197 A1 | 12/2010 | Higashiguchi et al. |
| 2011/0218154 A1 | 9/2011 | Schreiber et al. |
| 2011/0280849 A1 | 11/2011 | Zhang et al. |
| 2012/0121502 A1 | 5/2012 | Van Duzer et al. |
| 2013/0177642 A1 | 7/2013 | Zeldis |
| 2013/0225543 A1 | 8/2013 | Jones et al. |
| 2014/0011767 A1 | 1/2014 | Yang et al. |
| 2014/0142104 A1 | 5/2014 | van Duzer et al. |
| 2014/0142117 A1 | 5/2014 | van Duzer et al. |
| 2014/0243345 A1 | 8/2014 | van Duzer et al. |
| 2014/0249148 A1 | 9/2014 | van Duzer et al. |
| 2014/0357512 A1 | 12/2014 | Yang et al. |

(Continued)

FOREIGN PATENT DOCUMENTS

| | | |
|---|---|---|
| EP | 2 524 918 A1 | 11/2012 |
| WO | 1998/003502 A1 | 1/1998 |

(Continued)

OTHER PUBLICATIONS

Angibaud et al. (2005) "Discovery of Pyrimidyl-5-hydroxamic acids as New Potent Histone Deacetylase Inhibitors," European Journal of Medicinal Chemistry. 40(6):597-606.

Brana et al. (2002) "Synthesis and biological evaluation of novel 2-(1H-imidazol-4-y0cyclopropane carboxylic acids: key intermediates for H3 histamine receptor ligands," BioOrganic & Medicinal Chemistry Letter. 12(24):3561-3563.

Broxterman et al. (1992) "Synthesis of (optically active) sulfur-containing trifunctional amino acids by radical addition to (optically active) unsaturated amino acids," The Journal of Organic Chemistry. 57(23):6286-6294.

Butler et al. (2000) "Suberoylanilide Hydroxamic Acid, an Inhibitor of Histone Deacetylase, Suppresses the Growth of Prostate Cancer Cells in Vitro and in Vivo," Cancer Research. 60:5165-5170.

Carey et al. (2006) "Histone deacetylase inhibitors: gathering pace," Current Opinion in Pharmacology. 6:369-375.

(Continued)

*Primary Examiner* — Kortney L. Klinkel
*Assistant Examiner* — Tori M Strong
(74) *Attorney, Agent, or Firm* — Lathrop Gage LLP; Brian C. Trinque

(57) ABSTRACT

The invention relates to combinations comprising an HDAC inhibitor and an immunomodulatory drug for the treatment of lymphoma in a subject in need thereof. Also provided herein are methods for treating lymphoma in a subject in need thereof comprising administering to the subject an effective amount of one of the above combinations.

7 Claims, 9 Drawing Sheets

(56) References Cited

U.S. PATENT DOCUMENTS

| | | |
|---|---|---|
| 2015/0045380 A1 | 2/2015 | van Duzer et al. |
| 2015/0099744 A1 | 4/2015 | Tamang et al. |
| 2015/0105358 A1 | 4/2015 | Quayle et al. |
| 2015/0105383 A1 | 4/2015 | Quayle et al. |
| 2015/0105384 A1 | 4/2015 | Jones et al. |
| 2015/0105409 A1 | 4/2015 | Quayle et al. |
| 2015/0119413 A1 | 4/2015 | Gradilone et al. |
| 2015/0150871 A1 | 6/2015 | Quayle et al. |
| 2015/0176076 A1 | 6/2015 | Yang et al. |
| 2015/0239869 A1 | 8/2015 | Mazitschek et al. |
| 2015/0250786 A1 | 9/2015 | Berton et al. |
| 2015/0299130 A1 | 10/2015 | van Duzer et al. |
| 2015/0359794 A1 | 12/2015 | Benz et al. |
| 2016/0030458 A1 | 2/2016 | Jones et al. |
| 2016/0067259 A1 | 3/2016 | van Duzer et al. |
| 2016/0137630 A1 | 5/2016 | Shearstone et al. |
| 2016/0158231 A1 | 6/2016 | Jarpe et al. |
| 2016/0158232 A1 | 6/2016 | Pozzi et al. |
| 2016/0168093 A1 | 6/2016 | van Duzer et al. |

FOREIGN PATENT DOCUMENTS

| | | | |
|---|---|---|---|
| WO | 2001/070675 A2 | 9/2001 | |
| WO | WO 02064083 A2 * | 8/2002 | ........... A61K 31/454 |
| WO | 2002/074298 A1 | 9/2002 | |
| WO | 2003/037869 A1 | 5/2003 | |
| WO | 2003/076401 A1 | 9/2003 | |
| WO | 2003/076430 A1 | 9/2003 | |
| WO | 2004/052869 A1 | 6/2004 | |
| WO | 2005/012261 A1 | 2/2005 | |
| WO | 2005/028447 A1 | 3/2005 | |
| WO | 2005/030705 A1 | 4/2005 | |
| WO | 2006/102557 A2 | 9/2006 | |
| WO | 2006/123121 A1 | 11/2006 | |
| WO | 2007/022638 A1 | 3/2007 | |
| WO | 2007/091703 A2 | 8/2007 | |
| WO | 2007/130429 A2 | 11/2007 | |
| WO | 2007/144341 A1 | 12/2007 | |
| WO | 2008/003801 A1 | 1/2008 | |
| WO | 2008/033746 A2 | 3/2008 | |
| WO | 2008/055068 A2 | 5/2008 | |
| WO | 2008/091349 A1 | 7/2008 | |
| WO | 2009/137462 A1 | 11/2009 | |
| WO | 2009/137503 A1 | 11/2009 | |
| WO | 2010/009155 A2 | 1/2010 | |
| WO | 2010/011296 A2 | 1/2010 | |
| WO | 2010/080996 A1 | 7/2010 | |
| WO | 2010/131922 A2 | 11/2010 | |
| WO | 2011/011186 A1 | 1/2011 | |
| WO | 2011/019393 A2 | 2/2011 | |
| WO | 2011/084991 A2 | 7/2011 | |
| WO | 2011/091213 A2 | 7/2011 | |
| WO | WO 2011091213 A2 * | 7/2011 | ........... C07C 259/06 |
| WO | 2011/146855 A1 | 11/2011 | |
| WO | 2012/068109 A2 | 5/2012 | |
| WO | 2013/013113 A2 | 1/2013 | |
| WO | 2013/041480 A1 | 3/2013 | |

OTHER PUBLICATIONS

Chuang et al. (2009) "Multiple roles of HDAC inhibition in neurodegenerative conditions," Trends in Neurosciences. 32(11):591-601.
ClinicalTrials.gov "ACY-1215 (Ricolinostat) in Combination with Pomalidomide and Low-dose Dex in Relapsed-and-Refratory Multiple Myeloma," U.S. National Institutes of Health. Identifier: NCT01997840. Accessible on the Internet at URL: https://clinicaltrials.govict2/show/NCT01997840?term=ricolinostat&rank=1. [Last Accessed Oct. 22, 2015].
ClinicalTrials.gov "Phase Ib Study Evaluating ACY-1215 (Ricolinostat) in Combination with Pomalidomide and Dexamethasone in Relapsed or Relapsed-and-Refractory Multiple Myeloma," U.S. National Institutes of Health. Identifier: NCT02189343. Accessible on the Internet at URL: https://clinicaltrials.govict2/show/NCT02189343?term=ricolinostat&rank=2. [Last Accessed Oct. 22, 2015].
ClinicalTrials.gov "Study of ACY-1215 in Combination with Lenalidomide, and Dexamethasone in Multiple Myeloma," U.S. National Institutes of Health. Identifier: NCT01583283. Accessible on the Internet at URL: https://clinicaltrials.gov/ct2/show/NCT01583283?term=ricolinostat&rank=6. [Last Accessed Oct. 22, 2015].
Costello et al. (Dec. 2012) "Evidence for Changes in RREB-1, ZIP3, and Zinc in the Early Development of Pancreatic Adenocarcinoma," J. Gastrointest. Canc. 43:570-578.
Dallavalle et al. (2012) "Development and therapeutic impact of HDAC6-selective inhibitors," Biochemical Pharmacology. 84:756-765.
Dokmanovic et al. (2007) "Histone Deacetylase Inhibitors: Overview and Perspectives," Mol. Cancer Res. 5(10):981-989.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Giannini et al. (Jul. 2012) "Histone Deacetylase Inhibitors in the Treatment of Cancer: Overview and Perspectives," Future Med. Chem. 4(11):1439-1460.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Holford et al. (1981) "Understanding the dose-effect relationship: clinical application of pharmacokinetic-pharmacodynamic models," Clin. Pharmacokinet. 6:429-453.
Holien et al. (Sep. 20, 2012) "Addiction to c-MYC in multiple myeloma," Blood. 120:2450-2453.
Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.
Lane et al. (2009) "Histone Deacetylase Inhibitors in Cancer Therapy," J. Clin. Oncol. 27:5459-5468.
Loewe et al. (1926) "Uber Kombinationswirkungen," Arch. Exp. Pathol. Pharmacol. 114:313-326.—English Abstract Only.
Loudni et al. (2007) "Design, synthesis and biological evaluation of 1, 4-benzodiazepine-2, 5-dione-based HDAC inhibitors," Bioorganic and Medicinal Chemistry Letters. 17:4819-4823.
Mazitschek et al. (2008) "Development of a Fluorescence Polarization Based Assay for Histone Deacetylase Ligand Discovery," Bioorganic and Medicinal Chemistry Letters. 18(9):2809-2812.
Miller et al. (1998) "Paclitaxel as the Initial Treatment of Multiple Myeloma: An Eastern Cooperative Oncology Group Study (E1A93)," Am. J. Clin. Oncol. 21(6):553-556.
Neidle, Stephen: Ed. (2008) Cancer Drug Design and Discovery. Elsevier/Academic Press. pp. 427-431.
Neri et al. (2008) "In vivo anti-myeloma activity and modulation of gene expression profile induced by valproic acid, a histone deacetylase inhibitor," Journal of Haematology. 143:520-531.
Pellicciari et al. (1996) "Synthesis and Pharmacological Characterization of All Sixteen Stereoisomers of 2-(ZCarboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Perez (1998) "Paclitaxel in Breast Cancer," The Oncologist. 3:373-389.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Raje et al. (Dec. 8, 2011) "Rocilinostat (ACY-1215), a Selective HDAC6 Inhibitor, Alone and in Combination with Bortezomib in

(56) References Cited

OTHER PUBLICATIONS

Multiple Myeloma: Preliminary Results From the First-in-Humans Phase I/II Study," In; The 54th ASH Annual Meeting and Exposition. Paper No. 4061. Retreived Online at https://ash.confex.com/ash/2012/webprogram/Paper52013.html.—Abstract Only.

Raje et al. (Jun. 2014) "Ricolinostat (ACY-1215), the first selective histone deacetylase 6 inhibitor, is active and well tolerated in combination with lenalidomide or bortezomib in patients with Refractory myeloma," Haematologica. 99(s1) Paper No. 258. pp. 110-111.

Richter et al. (Dec. 2011) "Salvage Therapy with Vorinostat, Lenalidomide, and Dexamethasone (ZRD) in Lenalidomide/Dexamethasone Relapsed/Refractory Multiple Myeloma, Salvage Therapy with Vorinostat, Lenalidomide, and Dexamethasone (ZRD) in Lenalidomide/Dexamethasone Relapsed/Refractory Multiple Myeloma," In; The 53rd ASH Annual Meeting and Exposition. Paper No. 3986. Retreived Online at https://ash.confex.com/ash/2011/webprogram/Paper43422.html.—Abstract Only.

Ropero et al. (2007) "The Role of Histone Deacetylases (HDACs) in Human Cancer," Molecular Oncology. 1:19-25.

Shaffer et al. (2008) "IRF4 addiction in multiple myeloma," Nature. 454:226-231.

Smil et al. (2009) "Novel HDAC6 Isoform Selective Chiral Small Molecule Histone Deacetylase Inhibitors," Bioorganic and Medicinal Chemistry Letters. 19:688-692.

Sporn et al. (2000) "Chemoprevention of Cancer," Carcinogenesis. 21(3):525-530.

Thoppil et al. (Sep. 2011) "Terpenoids as Potential Chemopreventive and Therapeutic Agents in Liver Cancer," World J. Hepatol. 3(9):228-249.

Walbrick et al.(1968) "A general method for synthesizing optically active 1,3-disubstituted allene hydrocarbons," The Journal of the American Chemical Society. 90(11):2895-2901.

Warner et al. (1992) "Electron demand in the transition state of the cyclopropylidene to allene ring opening," The Journal of Organic Chemistry. 57(23):6294-6300.

International Preliminary Report on Patentability corresponding to International Patent Application No. PCT/US2011/060791, dated Jul. 22, 2014.

International Search Report with Written Opinion corresponding to International Patent Application No. PCT/US2011/021982, dated Oct. 10, 2011.

International Search Report with Written Opinion corresponding to International Patent Application No. PCT/US2011/060791, dated Mar. 5, 2014.

International Search Report with Written Opinion corresponding to International Patent Application No. PCT/US2014/059387, dated Feb. 5, 2015.

Search Opinion corresponding to European Patent Application No. 11735212, dated Jun. 26, 2014.

Supplementary European Search Report corresponding to European Application No. 11840803.8, dated Mar. 5, 2014.

Written Opinion corresponding to Singapore Patent Application No. Application No. 201205393-0, dated Nov. 15, 2013.

International Search Report with Written Opinion corresponding to International Search Report No. PCT/US2014/068263, dated Feb. 27, 2015.

Amengual (2012) "Dual Targeting of Protein Degradation Pathways with the Selective HDAC6 Inhibitor Rocilinostat (ACY-1215) and Bortezomib, Demonstrates Synergistic Antitumor Activity in Preclinical Models of Lymphoma," Blood. 120:1650.

Gardner et al. (2009) "A novel regimen of vorinostat with interferon gamma for refractory Sézary syndrome," J. Am. Acad. Dermatol. 61(1):112-116.

Genetic Engineering & Biotechnology News (Feb. 9, 2012) "Celgene Invests $15M in Acetylon to Support HDAC Inhibitor Development," Accessible on the Internet at URL: http://www.genengnews.com/gen-news-highlights/celgeneinvests-15m-in-acetylon-to-support-hdac-inhibitor-development/81246342. [Last Accessed Sep. 13, 2017], 1 pg.

Ghurye et al. (Aug. 22, 2013) "BET bromodomain inhibition by JQ1 suppresses interleukin-6 secretion in myeloma cells," In; The Frontiers in Immunology Conference Abstracts of the 15th International Congress of Immunology (ICI).

Lwin et al. (Nov. 1, 2013) "A microenvironment-mediated c-Myc/miR-548m/HDAC6 amplification loop in non-Hodgkin B cell lymphomas," J. Clin. Invest. 123(11):4612-4626.

Porcu et al. (2004) "Bexarotene-Induced T-Cell Immunomodulation and Response in CTCL," Blood. 104:744.

Sahakian et al. (2012) "Combination of ACY1215, a Selective Histone Deacetylase 6 (HDAC6) Inhibitor with the Bruton Tyrosine Kinase (BTK) Inhibitor, Ibrutinib, Represents a Novel Therapeutic Strategy in Mantle Cell Lymphoma (MCL)," Blood. 120:1660.

Scott et al. (2004) "Mitoxantrone: a review of its use in multiple sclerosis," CNS Drugs. 18(6):379-96.

Verhelle et al. (2007) "Lenalidomide and CC-4047 Inhibit the Proliferation of Malignant B Cells while Expanding Normal CD34+ Progenitor Cells," Cancer Res. 67(2):746-755.

* cited by examiner

Compound A + lenalidomide

Compound A + pomalidomide

Compound C + lenalidomide

Compound C + pomalidomide

Compound B + lenalidomide

Compound B + pomalidomide

Compound C + lenalidomide

Compound C + pomalidomide

COMBINATIONS OF HISTONE DEACETYLASE INHIBITORS AND IMMUNOMODULATORY DRUGS

CROSS-REFERENCE TO RELATED APPLICATIONS

This application claims priority to U.S. Provisional Application Ser. Nos. 61/911,086, filed Dec. 3, 2013, and 62/061,368, filed Oct. 8, 2014, each of which is incorporated herein by reference in its entirety.

BACKGROUND

Histone deacetylase (HDAC) enzymes represent attractive therapeutic targets in lymphoma, but unfortunately non-selective HDAC inhibitors have led to dose-limiting toxicities in patients.

The immunomodulatory (IMiD) class of drugs, including lenalidomide and pomalidomide, exhibit anti-lymphoma properties in a variety of lymphoma models, and have demonstrated clinical activity in lymphoma patients.

Due to the dose-limiting toxicities of the above therapies, there is an ongoing need in the art for more efficacious and less toxic compositions and methods for the treatment of lymphoma. In order to meet these needs, provided herein are pharmaceutical combinations comprising a HDAC inhibitor and an immunomodulatory drug, and methods for the treatment of lymphoma. The combinations and methods of the invention are well tolerated and do not exhibit the dose-limiting toxicities of prior therapies.

SUMMARY OF THE INVENTION

Provided herein are pharmaceutical combinations for the treatment of lymphoma in a subject in need thereof. Also provided herein are methods for treating lymphoma in a subject in need thereof.

Provided in some embodiments are combinations comprising a histone deacetylase (HDAC) inhibitor and an immunomodulatory drug (IMiD) for the treatment of lymphoma in a subject in need thereof. For example, an embodiment of the invention provides a pharmaceutical combination for treating lymphoma comprising a therapeutically effective amount of a histone deacetylase 6 (HDAC6) specific inhibitor or a pharmaceutically acceptable salt thereof, and an immunomodulatory drug (IMiD) or a pharmaceutically acceptable salt thereof. An additional embodiment of the invention provides a pharmaceutical combination for treating lymphoma comprising a therapeutically effective amount of a histone deacetylase 6 (HDAC6) specific inhibitor or a pharmaceutically acceptable salt thereof, and an immunomodulatory drug (IMiD) or a pharmaceutically acceptable salt thereof, wherein the combination is administered at dosages that would not be effective when one or both of the compounds are administered alone, but which amounts are effective in combination.

Provided in other embodiments are methods for treating lymphoma in a subject in need thereof comprising administering to the subject an effective amount of a combination comprising a histone deacetylase (HDAC) inhibitor and an immunomodulatory drug (MD). For example, an embodiment of the invention provides a method for treating lymphoma in a subject in need thereof comprising administering to the subject a therapeutically effective amount of a pharmaceutical combination comprising a histone deacetylase 6 (HDAC6) specific inhibitor or a pharmaceutically acceptable salt thereof, and an immunomodulatory drug (IMiD) or a pharmaceutically acceptable salt thereof.

In specific embodiments, the HDAC6 specific inhibitor is a compound of Formula I:

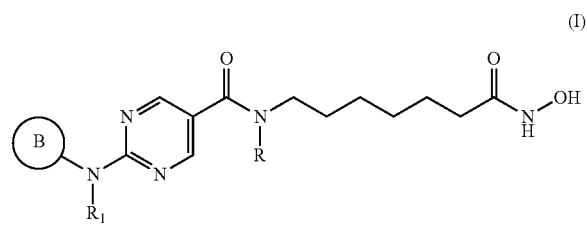

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

In preferred embodiments, the compound of Formula I is:

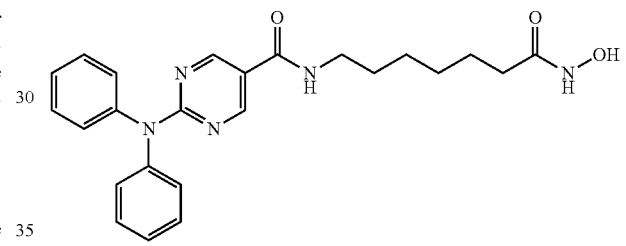

or a pharmaceutically acceptable salt thereof.

In yet other embodiments, the compound of Formula I is:

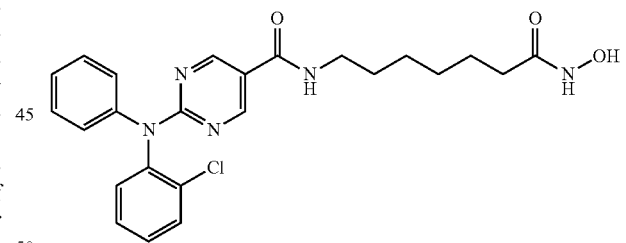

or a pharmaceutically acceptable salt thereof.

In other specific embodiments, the HDAC6 specific inhibitor is a compound of Formula II:

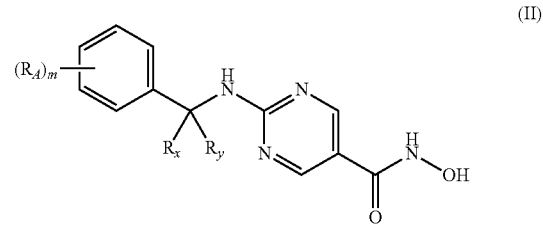

(II)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_4$ is independently $C_{1-6}$-alkyl, $C_{1-6}$-alkoxy, halo, OH, —$NO_2$, —CN, or —$NH_2$;

and m is 0, 1, or 2.

In preferred embodiments, the compound of Formula II is:

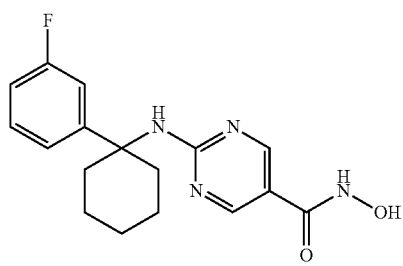 [SMILES: O=C(NO)c1cnc(NC2(c3cccc(F)c3)CCCCC2)nc1]

or a pharmaceutically acceptable salt thereof.

In other preferred embodiments, the compound of Formula II is:

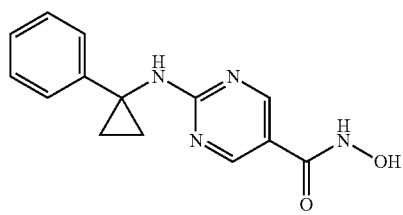 [SMILES: O=C(NO)c1cnc(NC2(c3ccccc3)CC2)nc1]

or a pharmaceutically acceptable salt thereof.

In some embodiments of the combinations and/or methods, the immunomodulatory drug is a compound of Formula III:

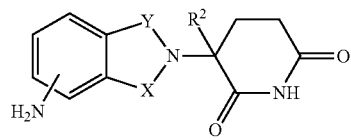

or a pharmaceutically acceptable salt thereof, wherein, one of X and Y is C=O, the other of X and Y is $CH_2$ or C=O; and $R^2$ is H or $C_{1-6}$-alkyl.

In preferred embodiments, the compound of Formula III is:

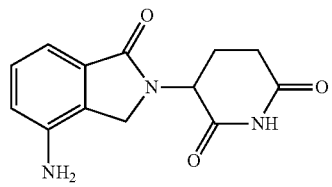

or a pharmaceutically acceptable salt thereof.

In yet other preferred embodiments, the compound of Formula III is:

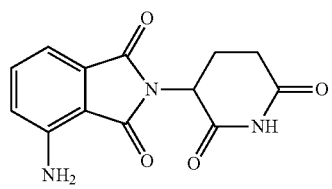

or a pharmaceutically acceptable salt thereof.

In some embodiments, the HDAC inhibitor and the immunomodulatory drug are administered with a pharmaceutically acceptable carrier.

In some embodiments, the HDAC inhibitor and the immunomodulatory drug are administered in separate dosage forms. In other embodiments, the HDAC inhibitor and the immunomodulatory drug are administered in a single dosage form.

In some embodiments, the HDAC inhibitor and the immunomodulatory drug are administered at different times. In other embodiments, the HDAC inhibitor and the immunomodulatory drug are administered at substantially the same time.

In some embodiments, the combination of a HDAC inhibitor and an IMiD achieves a synergistic effect in the treatment of the subject in need thereof.

In some embodiments of the combinations and/or methods, the HDAC6 specific inhibitor is a compound of Formula I:

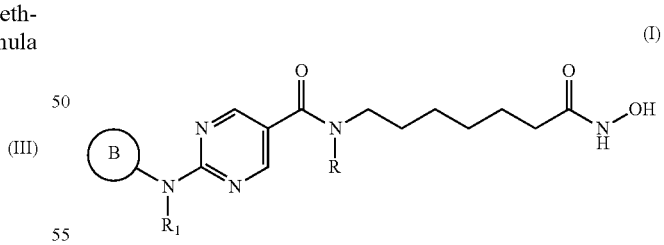

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl; and the immunomodulatory drug is a compound of Formula III:

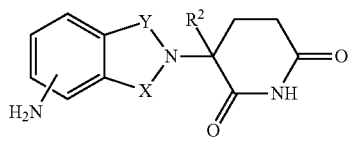

(III)

or a pharmaceutically acceptable salt thereof,
wherein,
one of X and Y is C=O, the other of X and Y is CH$_2$ or C=O; and
R$^2$ is H or C$_{1-6}$-alkyl.

In specific embodiments of the combinations and/or methods, the HDAC6 specific inhibitor is:

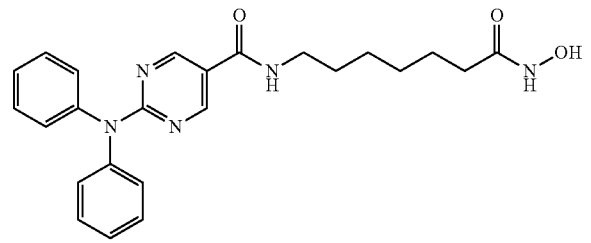 [SMILES: O=C(CCCCCCNC(=O)c1cnc(N(c2ccccc2)c2ccccc2)nc1)NO]

or a pharmaceutically acceptable salt thereof; and
the immunomodulatory drug is:

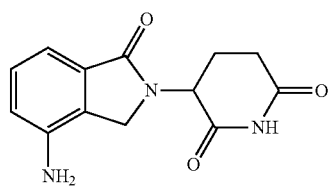 [SMILES: Nc1cccc2c1CN(C1CCC(=O)NC1=O)C2=O]

or a pharmaceutically acceptable salt thereof.

In specific embodiments of the combinations and/or methods, the HDAC6 specific inhibitor is:

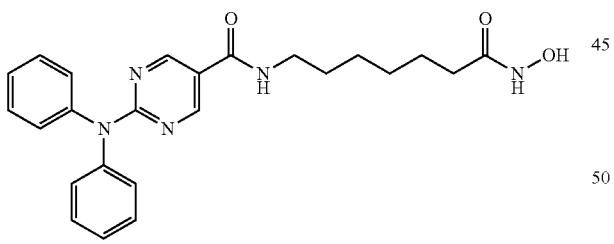

or a pharmaceutically acceptable salt thereof; and
the immunomodulatory drug is:

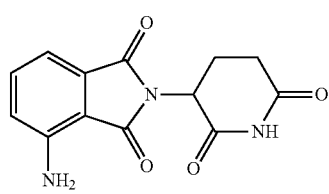 [SMILES: Nc1cccc2c1C(=O)N(C1CCC(=O)NC1=O)C2=O]

or a pharmaceutically acceptable salt thereof.

In specific embodiments of the combinations and/or methods, the HDAC6 specific inhibitor is:

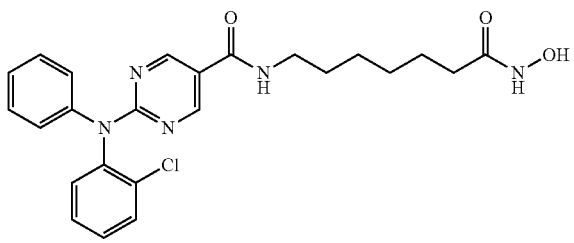 [SMILES: O=C(CCCCCCNC(=O)c1cnc(N(c2ccccc2)c2ccccc2Cl)nc1)NO]

or a pharmaceutically acceptable salt thereof; and
the immunomodulatory drug is:

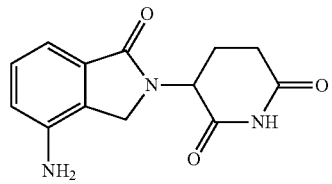 [SMILES: Nc1cccc2c1CN(C1CCC(=O)NC1=O)C2=O]

or a pharmaceutically acceptable salt thereof.

In specific embodiments of the combinations and/or methods, the HDAC6 specific inhibitor is:

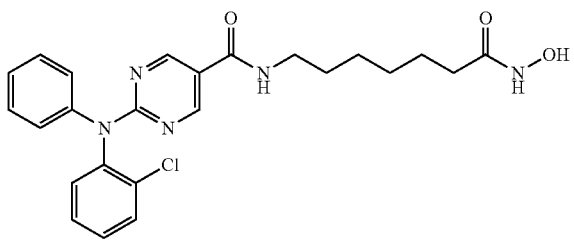 [SMILES: O=C(CCCCCCNC(=O)c1cnc(N(c2ccccc2)c2ccccc2Cl)nc1)NO]

or a pharmaceutically acceptable salt thereof; and
the immunomodulatory drug is:

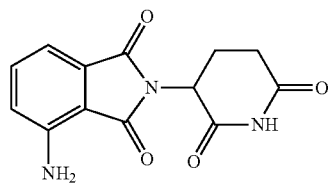 [SMILES: Nc1cccc2c1C(=O)N(C1CCC(=O)NC1=O)C2=O]

or a pharmaceutically acceptable salt thereof.

In some embodiments of the combinations and/or methods, the HDAC6 specific inhibitor is a compound of Formula II:

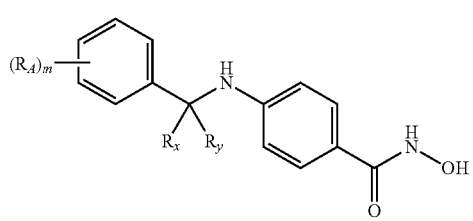

(II)

or a pharmaceutically acceptable salt thereof, wherein,
R$_x$ and R$_y$ together with the carbon to which each is attached, form a cyclopropyl, cyclobutyl, cyclopentyl, cyclohexyl, cycloheptyl, or cyclooctyl;
each R$_A$ is independently C$_{1-6}$-alkyl, C$_{1-6}$-alkoxy, halo, OH, —NO$_2$, —CN, or —NH$_2$;
and
m is 0, 1, or 2; and
the immunomodulatory drug is a compound of Formula III:

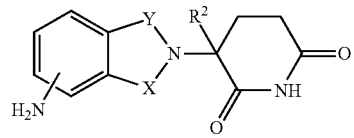

or a pharmaceutically acceptable salt thereof,
wherein,
one of X and Y is C=O, the other of X and Y is CH$_2$ or C=O; and
R$^2$ is H or C$_{1-6}$-alkyl.
In specific embodiments of the combinations and/or methods, the HDAC6 specific inhibitor is:

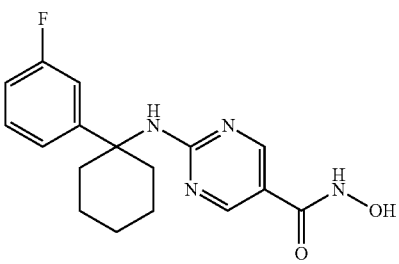 [SMILES: O=C(NO)c1cnc(NC2(c3cccc(F)c3)CCCCC2)nc1]

or a pharmaceutically acceptable salt thereof; and
the immunomodulatory drug is:

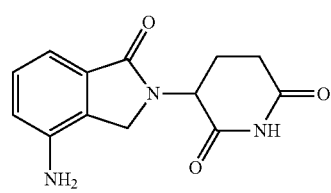 [SMILES: Nc1cccc2c1CN(C1CCC(=O)NC1=O)C2=O]

or a pharmaceutically acceptable salt thereof.
In specific embodiments of the combinations and/or methods, the HDAC6 specific inhibitor is:

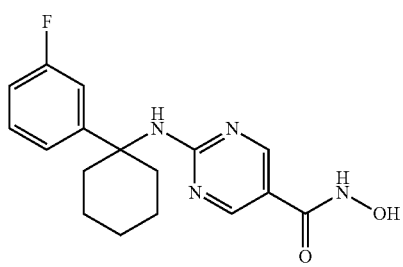 [SMILES: O=C(NO)c1cnc(NC2(c3cccc(F)c3)CCCCC2)nc1]

or a pharmaceutically acceptable salt thereof; and the immunomodulatory drug is:

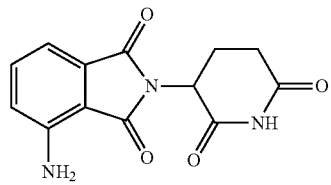

or a pharmaceutically acceptable salt thereof.
In specific embodiments of the combinations and/or methods, the HDAC6 specific inhibitor is:

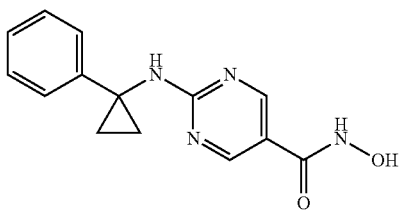 [SMILES: O=C(NO)c1cnc(NC2(c3ccccc3)CC2)nc1]

or a pharmaceutically acceptable salt thereof; and
the immunomodulatory drug is:

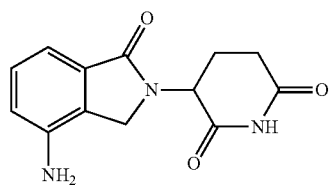

or a pharmaceutically acceptable salt thereof.
In specific embodiments of the combinations and/or methods, the HDAC6 specific inhibitor is:

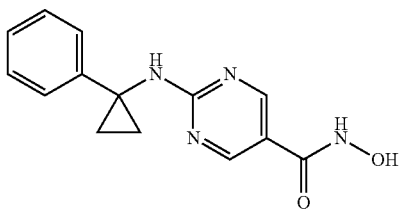 [SMILES: O=C(NO)c1cnc(NC2(c3ccccc3)CC2)nc1]

or a pharmaceutically acceptable salt thereof; and
the immunomodulatory drug is:

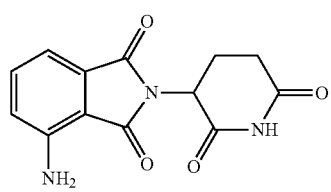 [SMILES: Nc1cccc2c1C(=O)N(C1CCC(=O)NC1=O)C2=O]

or a pharmaceutically acceptable salt thereof.

An embodiment of the invention includes a method for decreasing cell cycle progression by administering a combination comprising an HDAC inhibitor and an immunomodulatory drug.

Another embodiment of the invention includes a method for increasing cellular apoptosis by administering a combination comprising an HDAC inhibitor and an immunomodulatory drug.

A further embodiment of the invention includes a method for suppressing transcriptional regulators in cancer by administering a combination comprising an HDAC inhibitor and an immunomodulatory drug.

Other objects, features, and advantages will become apparent from the following detailed description. The detailed description and specific examples are given for illustration only because various changes and modifications within the spirit and scope of the invention will become apparent to those skilled in the art from this detailed description. Further, the examples demonstrate the principle of the invention.

BRIEF DESCRIPTION OF THE FIGURES

FIG. 1A shows the $F_A$/CI Synergy Plots after treatment of Mino MCL cells with Compound A, and either lenalidomide (top) or pomalidomide (bottom). FIG. 1B shows the $F_A$/CI Synergy Plots after treatment of Mino MCL cells with Compound B, and either lenalidomide (top) or pomalidomide (bottom). FIG. 1C shows the $F_A$/CI Synergy Plots after treatment of Mino MCL cells with Compound C, and either lenalidomide (top) or pomalidomide (bottom). FIG. 1D shows the $F_A$/CI Synergy Plots after treatment of Jeko1 MCL cells with Compound A and pomalidomide. FIG. 1E shows the $F_A$/CI Synergy Plots after treatment of Jeko1 MCL cells with Compound B, and either lenalidomide (top) or pomalidomide (bottom). FIG. 1F shows the $F_A$/CI Synergy Plots after treatment of Jeko1 MCL cells with Compound C, and either lenalidomide (top) or pomalidomide (bottom). Data points with Combination Index (CI) values <1 indicate treatment combinations resulting in synergistic decreases in cellular viability.

DETAILED DESCRIPTION

Figure 1A:
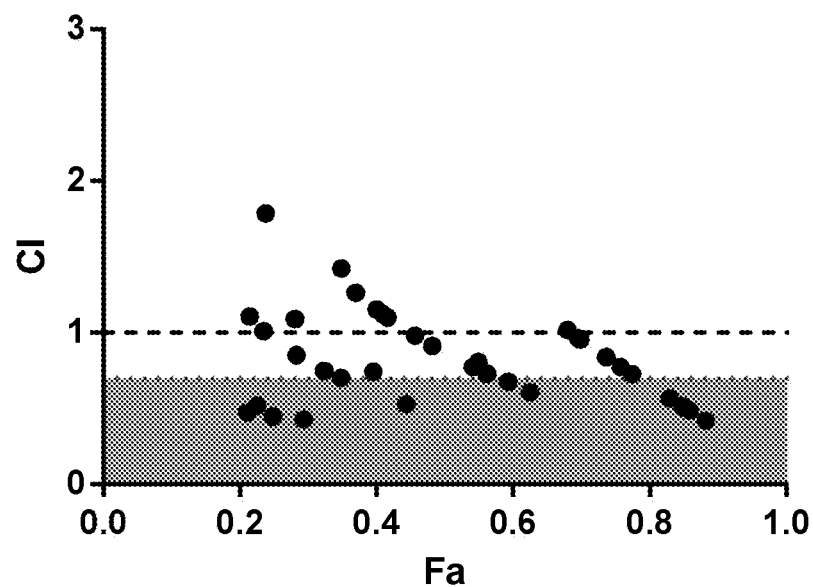
FIGS. 1A-F show the $F_A$/CI Synergy Plots after treatment of Mino Mantle Cell Lymphoma (MCL) cells with an HDAC6 inhibitor and an IMiD.
Figure 1A:
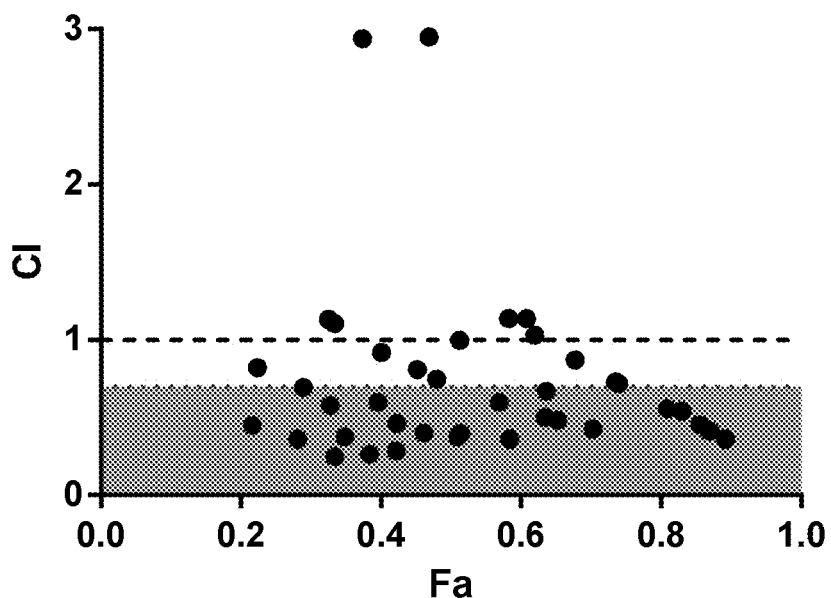
Figure 1B:
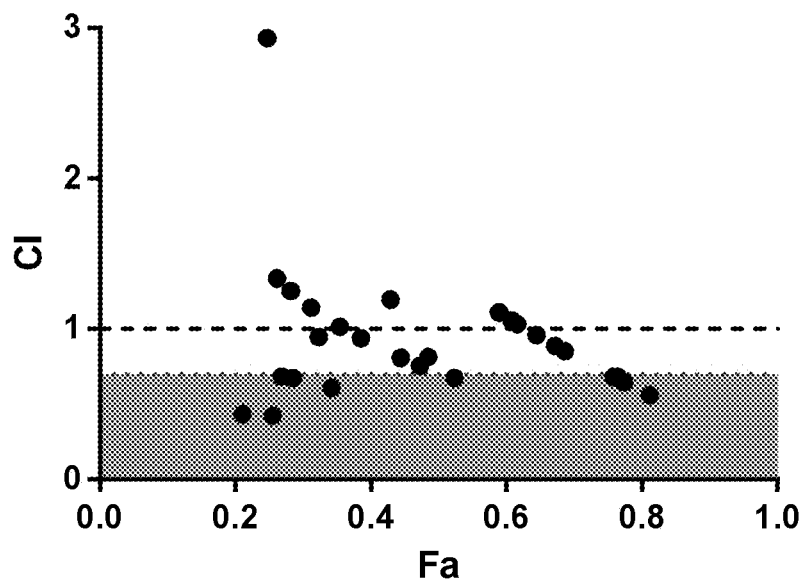
Figure 1B:
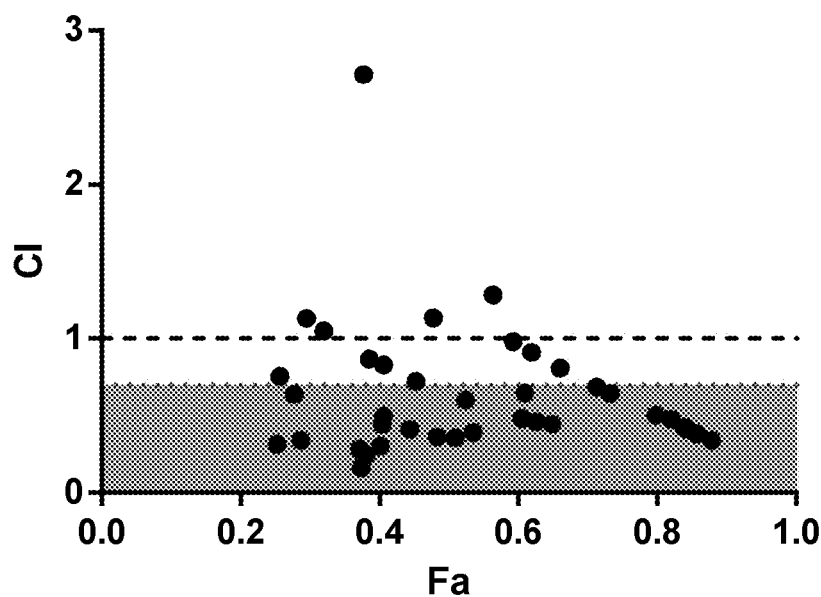
Figure 1C:
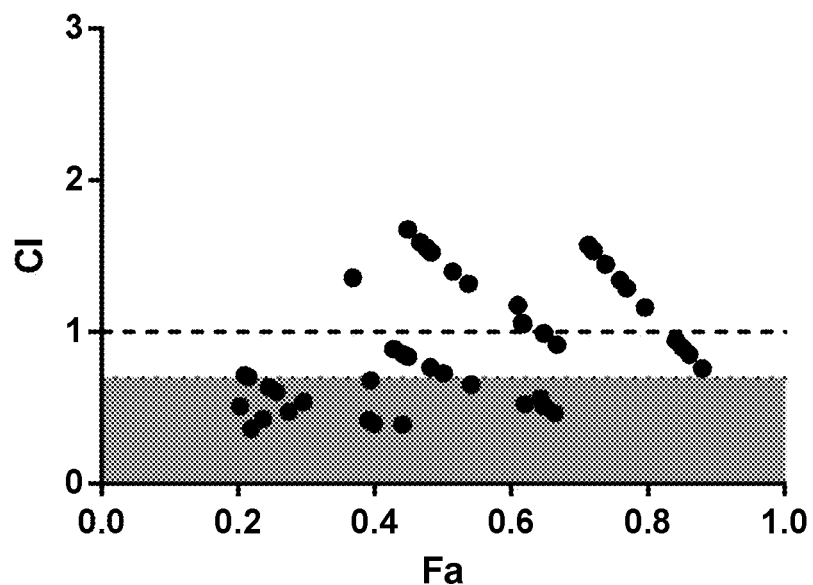
Figure 1C:
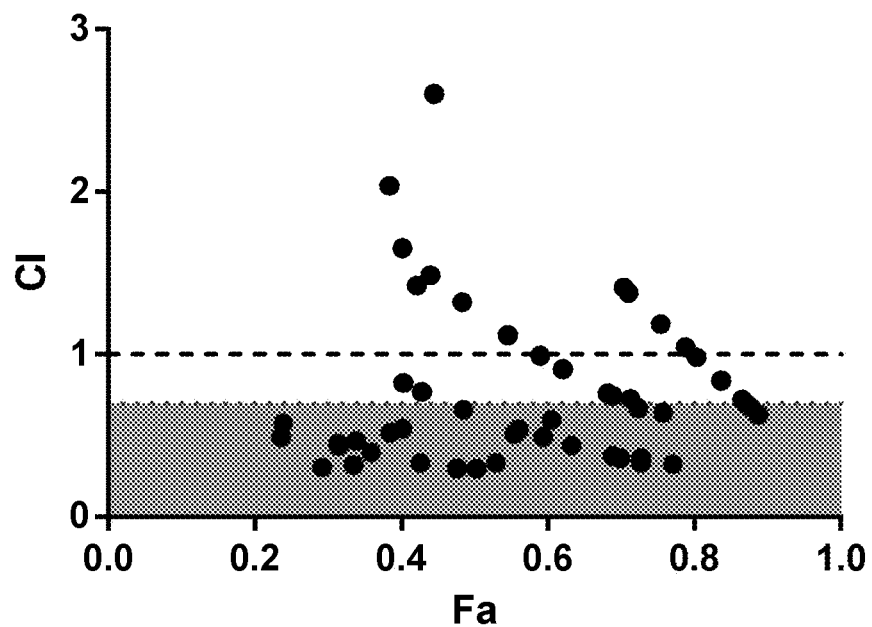
Figure 1D:
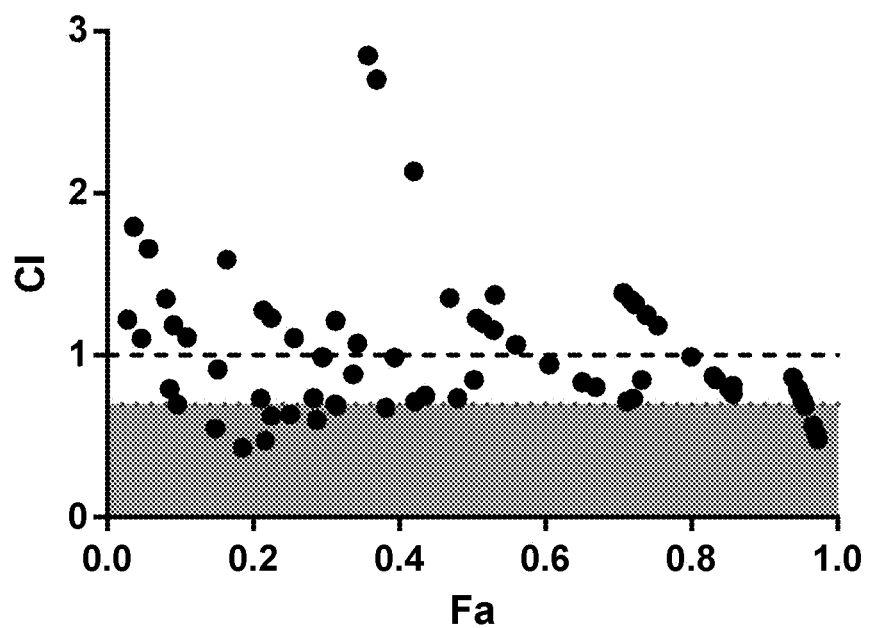
Figure 1E:
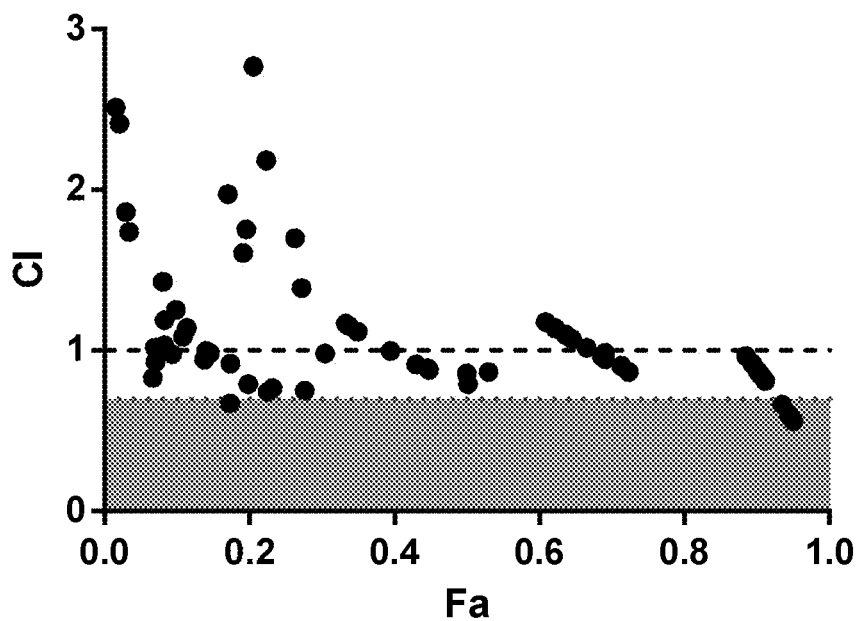
Figure 1E:
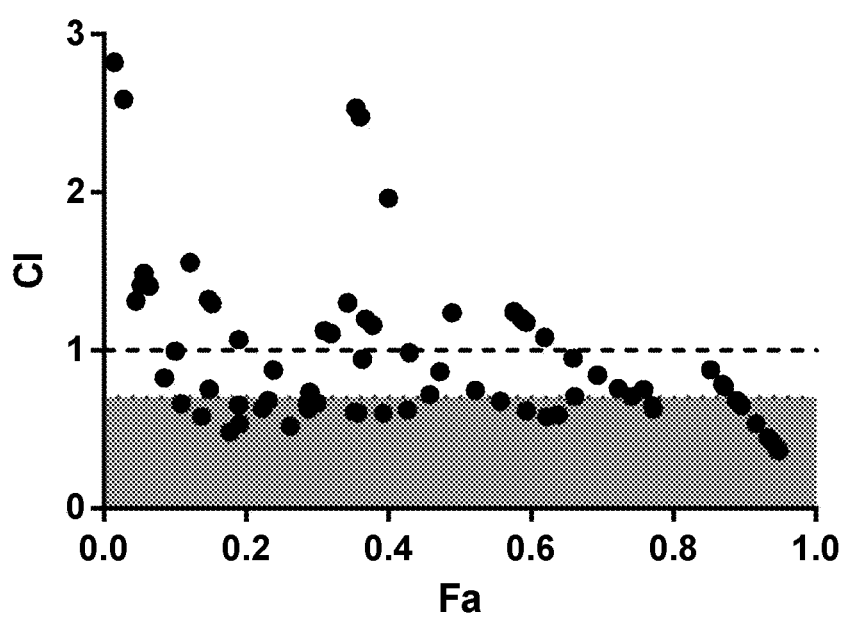
Figure 1F:
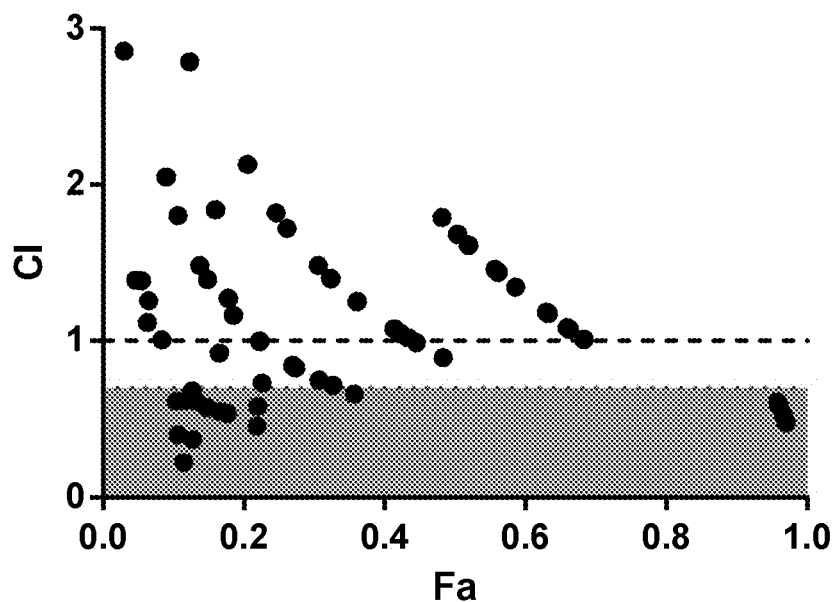
Figure 1F:
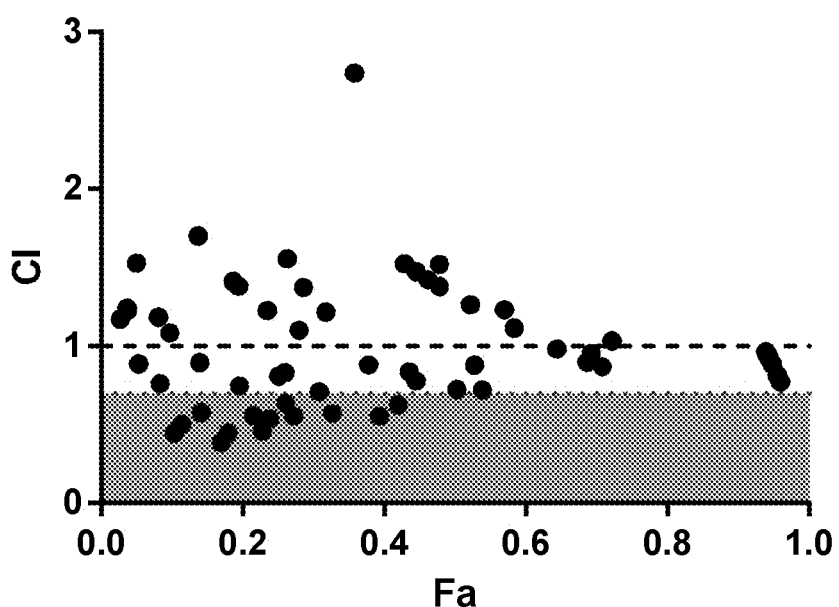

The instant application is directed, generally, to combinations comprising a histone deacetylase (HDAC) inhibitor and an immunomodulatory drug (IMiD), and methods for the treatment of lymphoma.

Definitions

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The terms "cycloalkyl" or "cycloalkylene" denote a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cycloheptyl, and cyclooctyl; and examples of $C_{3-12}$-cycloalkyl include, but are not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "halo" refers to a halogen, such as fluorine, chlorine, bromine, and iodine.

The term "combination" refers to two or more therapeutic agents to treat a therapeutic condition or disorder described in the present disclosure. Such combination of therapeutic agents may be in the form of a single pill, capsule, or intravenous solution. However, the term "combination" also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 specific" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 specific. On the other hand, a compound that binds to HDAC6 with an $IC_{50}$ of 50 nM and to HDAC1 with an $IC_{50}$ of 60 nM is not HDAC6 specific The term "inhibitor" is synonymous with the term antagonist.

Histone Deacetylase (HDAC) Inhibitors

Provided herein are pharmaceutical combinations for the treatment of lymphoma in a subject in need thereof. Also provided herein are methods for treating lymphoma in a subject in need thereof.

The combinations and methods of the invention comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 inhibitor.

In some embodiments, the HDAC6 specific inhibitor is a compound of Formula I:

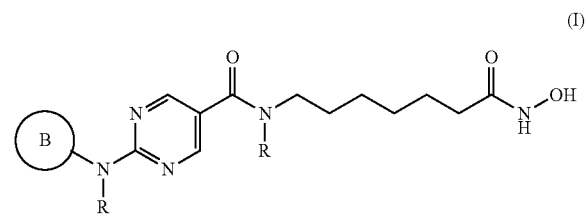

(I)

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl.

Representative compounds of Formula I include, but are not limited to:

Compound A

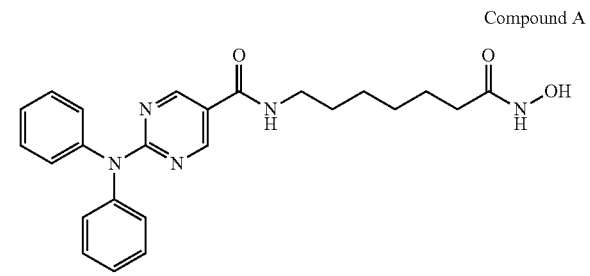

2-(diphenylamino)-N-(7-(hydroxyamino)-7-oxoheptyl)pyrimidine-5-carboxamide
$IC_{50}$(nM) HDAC6 = 10 HDAC3 = 84

Compound B

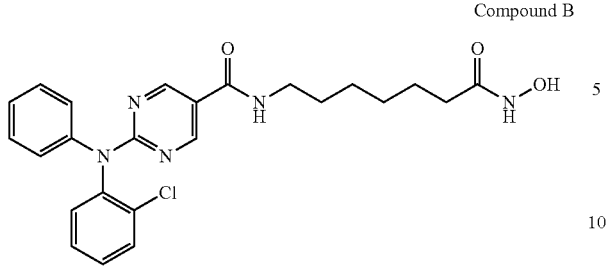

2-((2-chlorophenyl)(phenyl)amino)-N-(7-(hydroxyamino)-7-oxoheptyl)pyrimidine-5-carboxamide
IC$_{50}$(nM) HDAC6 = 4 HDAC3 = 76 or pharmaceutically acceptable sans thereof.

The preparation and properties of selective HDAC6 inhibitors according to Formula I are provided in International Patent Application No. PCT/US2011/021982, the entire contents of which is incorporated herein by reference.

In other embodiments, the HDAC6 specific inhibitor is a compound of Formula II:

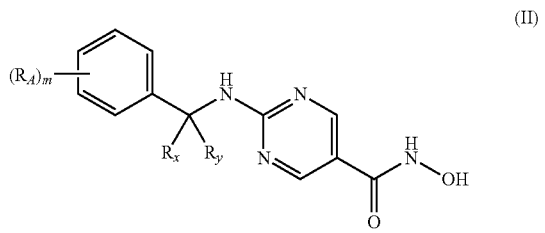

(II)

or a pharmaceutically acceptable salt thereof,
wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —NO$_2$, —CN, or —NH$_2$;
and
m is 0, 1, or 2.

Representative compounds of Formula II include, but are not limited to:

Compound C

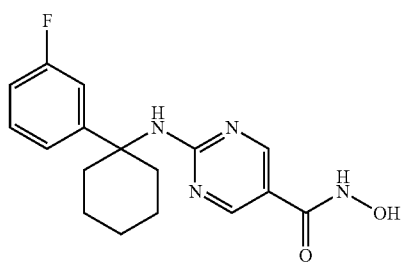

IC$_{50}$(nM) HDAC6 = 7 HDAC1 = 2123
(283.5x) HDAC2 = 2570 (9343.2x)
HDAC3 = 11223 (1498.8x)

Compound D

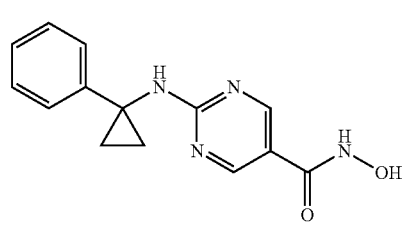

IC$_{50}$(nM) HDAC6 = 2 HDAC1 = 94 (60x)
HDAC2 = 128 (81.9x)
HDAC3 = 219 (139.5x)

or pharmaceutically acceptable salts thereof.

The preparation and properties of selective HDAC6 inhibitors according to Formula II are provided in International Patent Application No. PCT/US2011/060791, the entire contents of which are incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Immunomodulatory Drugs (IMiDs)

The combinations and methods of the invention comprise an immunomodulatory drug (IMiD). The IMiD may be any immunomodulatory drug. Preferably, the IMiD is a thalidomide of Formula III.

In some embodiments, the immunomodulatory drug is a compound of Formula

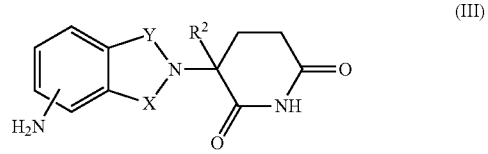

(III)

or a pharmaceutically acceptable salt thereof,
wherein,
one of X and Y is C=O, the other of X and Y is CH$_2$ or C=O; and R$^2$ is H or C$_{1-6}$-alkyl.

Representative compounds of Formula III include, but are not limited to:

Compound E

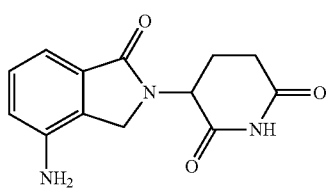

Compound F

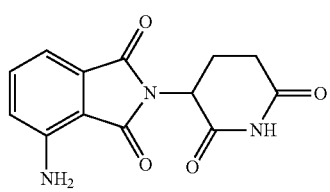

or pharmaceutically acceptable salts thereof.

The preparation and properties of the immunomodulatory drugs according to Formula III are provided in U.S. Pat. Nos. 5,635,517; 6,281,230; 6,335,349; and 6,476,052; as well as International Patent Application No. PCT/US97/013375, each of which is incorporated herein by reference in its entirety.

In some embodiments, the compounds described herein are unsolvated. In other embodiments, one or more of the compounds are in solvated form. As known in the art, the solvate can be any of pharmaceutically acceptable solvent, such as water, ethanol, and the like.

Combinations/Pharmaceutical Combinations

Provided herein are combinations for the treatment of lymphoma in a subject in need thereof. Provided in some embodiments are combinations comprising a histone deacetylase (HDAC) inhibitor and an immunomodulatory drug (IMiD) for the treatment of lymphoma in a subject in need thereof.

In some embodiments of the combinations, the HDAC inhibitor is an HDAC6 inhibitor.

In specific embodiments, the HDAC6 specific inhibitor is a compound of Formula I:

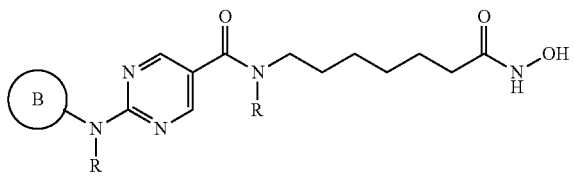

(I)

or a pharmaceutically acceptable salt thereof.

In preferred embodiments, the compound of Formula I is:

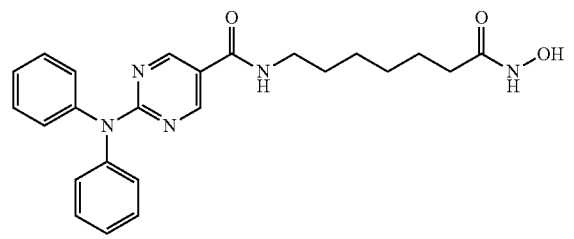 [SMILES: O=C(CCCCCCNC(=O)c1cnc(N(c2ccccc2)c2ccccc2)nc1)NO]

or a pharmaceutically acceptable salt thereof.

In yet other embodiments, the compound of Formula I is:

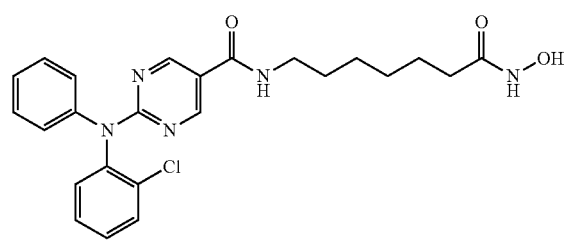 [SMILES: O=C(CCCCCCNC(=O)c1cnc(N(c2ccccc2)c2ccccc2Cl)nc1)NO]

or a pharmaceutically acceptable salt thereof.

In other specific embodiments, the HDAC6 specific inhibitor is a compound of Formula II:

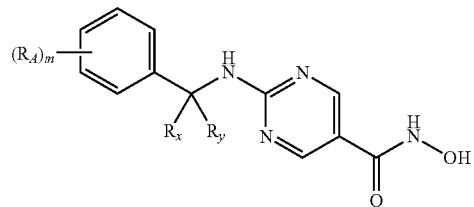

(II)

or a pharmaceutically acceptable salt thereof.

In preferred embodiments, the compound of Formula II is:

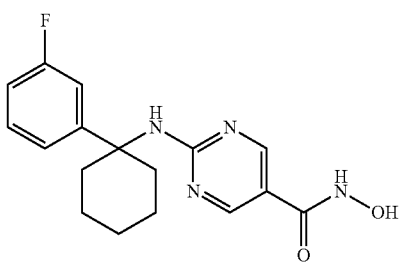 [SMILES: O=C(NO)c1cnc(NC2(c3cccc(F)c3)CCCCC2)nc1]

or a pharmaceutically acceptable salt thereof.

In other preferred embodiments, the compound of Formula II is:

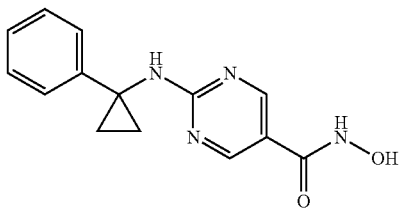 [SMILES: O=C(NO)c1cnc(NC2(c3ccccc3)CC2)nc1]

or a pharmaceutically acceptable salt thereof.

In some embodiments of the combinations, the immunomodulatory drug is a compound of Formula III:

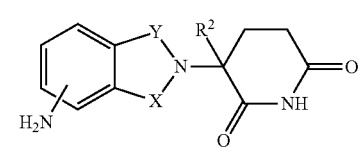

(III)

or a pharmaceutically acceptable salt thereof.

In preferred embodiments, the compound of Formula III is:

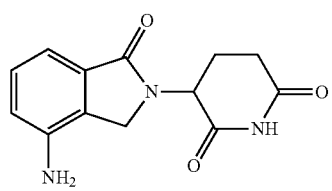 [SMILES: Nc1cccc2c1CN(C1CCC(=O)NC1=O)C2=O]

or a pharmaceutically acceptable salt thereof.

In yet other preferred embodiments, the compound of Formula III is:

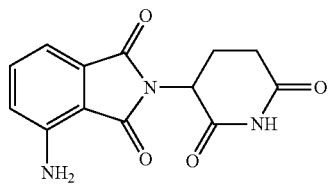 [SMILES: Nc1cccc2c1C(=O)N(C1CCC(=O)NC1=O)C2=O]

or a pharmaceutically acceptable salt thereof.

In one embodiment, provided herein is a combination therapy comprising an HDAC6 specific inhibitor and an immunomodulatory drug, wherein the HDAC6 specific inhibitor is a compound of Formula I:

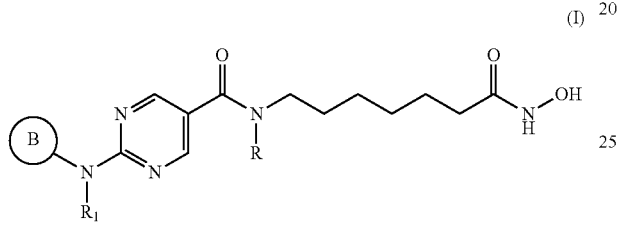

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl; and
the immunomodulatory drug is a compound of Formula III:

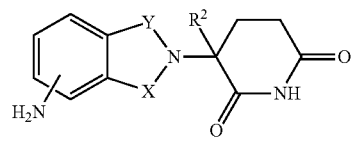

(III)

or a pharmaceutically acceptable salt thereof,
wherein,
one of X and Y is C=O, the other of X and Y is $CH_2$ or C=O; and
$R^2$ is H or $C_{1-6}$-alkyl.

In specific embodiments of the combinations, the HDAC6 specific inhibitor is:

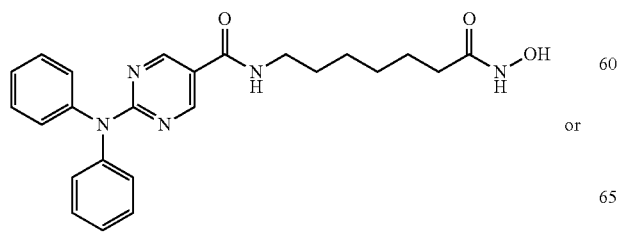

or

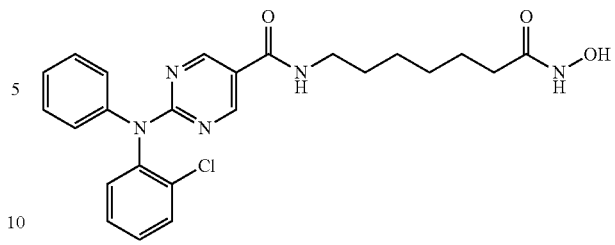

or pharmaceutically acceptable salts thereof; and
the immunomodulatory drug is:

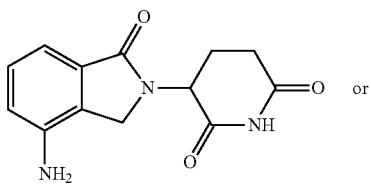

or

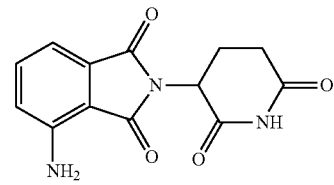

or a pharmaceutically acceptable salt thereof.

In another embodiment, provided herein is a combination therapy comprising an HDAC6 specific inhibitor and an immunomodulatory drug, wherein the HDAC6 specific inhibitor is a compound of Formula II:

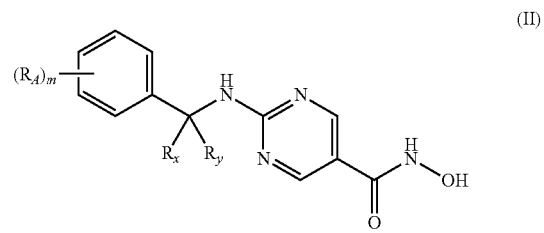

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$;
and
m is 0, 1, or 2; and
the immunomodulatory drug is a compound of Formula III:

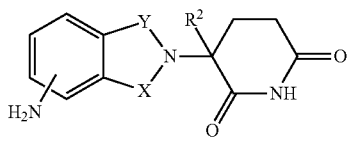

(III)

or a pharmaceutically acceptable salt thereof,
wherein,
one of X and Y is C=O, the other of X and Y is CH$_2$ or C=O; and
R$^2$ is H or C$_{1-6}$-alkyl.

In specific embodiments of the combinations, the HDAC6 specific inhibitor is:

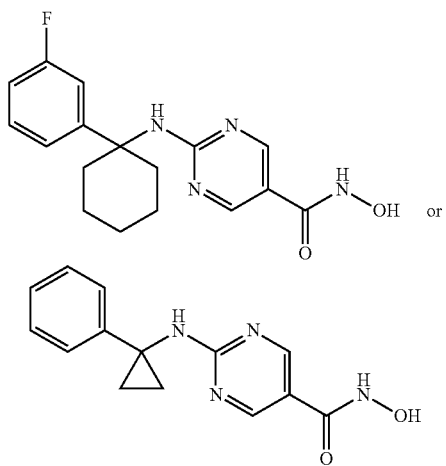

or a pharmaceutically acceptable salt thereof; and the immunomodulatory drug is:

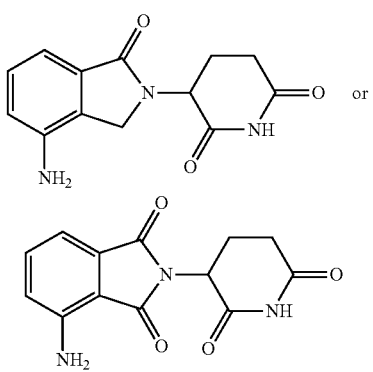

or a pharmaceutically acceptable salt thereof.

Although the compounds of Formulas I, II, and III are depicted in their neutral forms, in some embodiments, these compounds are used in a pharmaceutically acceptable salt form. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Administration/Dose

In some embodiments, the HDAC inhibitor (a compound of Formula I or II) is administered simultaneously with the immunomodulatory drug (a compound of Formula III). Simultaneous administration typically means that both compounds enter the patient at precisely the same time. However, simultaneous administration also includes the possibility that the HDAC inhibitor and the IMiD enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the HDAC inhibitor and the other of which contains the IMiD, can be employed. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising the IMiD.

In other embodiments, the HDAC inhibitor and the IMiD are not administered simultaneously. In some embodiments, the HDAC inhibitor is administered before the IMiD. In other embodiments, the IMiD is administered before the HDAC inhibitor. The time difference in non-simultaneous administrations can be greater than 1 minute, five minutes, 10 minutes, 15 minutes, 30 minutes, 45 minutes, 60 minutes, two hours, three hours, six hours, nine hours, 12 hours, 24 hours, 36 hours, or 48 hours. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and immunomodulatory drug are administered in a therapeutically effective amount or dosage. A "therapeutically effective amount" is an amount of HDAC6 inhibitor (a compound of Formula I or II) or an immunomodulatory drug (a compound of Formula III) that, when administered to a patient by itself, effectively treats the lymphoma. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC inhibitor and immunomodulatory drug are administered in a sub-therapeutically effective amount or dosage. A sub-therapeutically effective amount is an amount of HDAC inhibitor (a compound of Formula I or II) or an immunomodulatory drug (a compound of Formula III) that, when administered to a patient by itself, does not completely inhibit over time the biological activity of the intended target.

Whether administered in therapeutic or sub-therapeutic amounts, the combination of the HDAC inhibitor and the immunomodulatory drug should be effective in treating lymphoma. For example, a sub-therapeutic amount of a compound of Formula III (immunomodulatory drug) can be an effective amount if, when combined with a compound of Formula I or II (HDAC inhibitor), the combination is effective in the treatment of lymphoma.

In some embodiments, the combination of compounds exhibits a synergistic effect (i.e., greater than additive effect) in the treatment of the lymphoma. The term "synergistic effect" refers to the action of two agents, such as, for example, a HDAC inhibitor and an IMiD, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In different embodiments, depending on the combination and the effective amounts used, the combination of compounds can inhibit cancer growth, achieve cancer stasis, or even achieve substantial or complete cancer regression.

While the amounts of a HDAC inhibitor and an IMiD should result in the effective treatment of lymphoma, the amounts, when combined, are preferably not excessively toxic to the patient (i.e., the amounts are preferably within toxicity limits as established by medical guidelines). In some embodiments, either to prevent excessive toxicity and/or provide a more efficacious treatment of lymphoma, a limitation on the total administered dosage is provided. Typically, the amounts considered herein are per day; however, half-day and two-day or three-day cycles also are considered herein.

Different dosage regimens may be used to treat lymphoma. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day. In some embodiments, each dosage contains both an HDAC inhibitor and an IMiD to be delivered as a single dosage, while in other embodiments, each dosage contains either a HDAC inhibitor and an IMiD to be delivered as separate dosages.

Compounds of Formula I, II, or III, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and the IMiD of the pharmaceutical combination can be administered in a single unit dose or separate dosage forms. Accordingly, the phrase "pharmaceutical combination" includes a combination of two drugs in either a single dosage form or a separate dosage forms, i.e., the pharmaceutically acceptable carriers and excipients described throughout the application can be combined with an HDAC inhibitor and an IMiD in a single unit dose, as well as individually combined with a HDAC inhibitor and an IMiD when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or immunomodulatory drugs described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed., (Mack Publishing Company, Easton, Pa., 1990).

Methods of Treatment

The invention relates to methods for treating lymphoma in a subject in need thereof comprising administering to the subject a pharmaceutical combination of the invention. Thus, provided herein are methods for treating lymphoma in a subject in need thereof comprising administering to the subject a therapeutically effective amount of a combination comprising an HDAC inhibitor and an immunomodulatory drug.

The subject considered herein is typically a human. However, the subject can be any mammal for which treatment is desired. Thus, the methods described herein can be applied to both human and veterinary applications.

The terms "treating" or "treatment" indicates that the method has, at the least, mitigated abnormal cellular proliferation. For example, the method can reduce the rate of lymphoma growth in a patient, or prevent the continued growth or spread of the lymphoma, or even reduce the overall reach of the lymphoma.

As such, in one embodiment, provided herein is a method for treating lymphoma in a subject in need thereof comprising administering to the subject a therapeutically effective amount of Compound A, or a pharmaceutically acceptable salt thereof, and Compound E, or a pharmaceutically acceptable salt thereof.

In another embodiment is a method for treating lymphoma in a subject in need thereof comprising administering to the subject a therapeutically effective amount of Compound A, or a pharmaceutically acceptable salt thereof, and Compound F, or a pharmaceutically acceptable salt thereof.

In another embodiment is a method for treating lymphoma in a subject in need thereof comprising administering to the subject a therapeutically effective amount of Compound B, or a pharmaceutically acceptable salt thereof, and Compound E, or a pharmaceutically acceptable salt thereof.

In another embodiment is a method for treating lymphoma in a subject in need thereof comprising administering to the subject a therapeutically effective amount of Compound B, or a pharmaceutically acceptable salt thereof, and Compound F, or a pharmaceutically acceptable salt thereof.

In another embodiment is a method for treating lymphoma in a subject in need thereof comprising administering to the subject a therapeutically effective amount of Compound C, or a pharmaceutically acceptable salt thereof, and Compound E, or a pharmaceutically acceptable salt thereof.

In another embodiment is a method for treating lymphoma in a subject in need thereof comprising administering to the subject a therapeutically effective amount of Compound C, or a pharmaceutically acceptable salt thereof, and Compound F, or a pharmaceutically acceptable salt thereof.

In another embodiment is a method for treating lymphoma in a subject in need thereof comprising administering to the subject a therapeutically effective amount of Compound D, or a pharmaceutically acceptable salt thereof, and Compound E, or a pharmaceutically acceptable salt thereof.

In another embodiment is a method for treating lymphoma in a subject in need thereof comprising administering to the subject a therapeutically effective amount of Compound D, or a pharmaceutically acceptable salt thereof, and Compound F, or a pharmaceutically acceptable salt thereof.

In some embodiments of the methods, the subject was previously refractory to an immunomodulatory drug.

The invention relates to methods for decreasing cell cycle progression by administering a combination comprising an HDAC inhibitor and an immunomodulatory drug.

The invention relates to methods for increasing cellular apoptosis by administering a combination comprising an HDAC inhibitor and an immunomodulatory drug.

The invention relates to methods for suppressing transcriptional regulators in cancer by administering a combination comprising an HDAC inhibitor and an immunomodulatory drug.

Kits

In other embodiments, kits are provided. Kits according to the invention include package(s) comprising compounds or compositions of the invention. In some embodiments, kits comprise a HDAC inhibitor, or a pharmaceutically acceptable salt thereof, and an IMiD or a pharmaceutically acceptable salt thereof.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the invention to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substitutents, derivatives, formulations and/or methods of the invention may be made without departing from the spirit of the invention and the scope of the appended claims. Definitions of the variables in the structures in the schemes herein are commensurate with those of corresponding positions in the formulae presented herein.

The synthesis of the compounds of Formula I is provided in PCT/US2011/021982, which is incorporated herein by reference in its entirety. The synthesis of compounds of Formula II is provided in PCT/US2011/060791, which is incorporated herein by reference in its entirety. The synthesis of the compounds of Formula III is provided in U.S. Pat. Nos. 5,635,517; 6,281,230; 6,335,349; and 6,476,052; and in International Patent Application No. PCT/US97/013375, each of which is incorporated herein by reference in its entirety.

Example 1: Synthesis of 2-(diphenylamino)-N-(7-(hydroxyamino)-7-oxoheptyl)pyrimidine-5-carboxamide (Compound A)

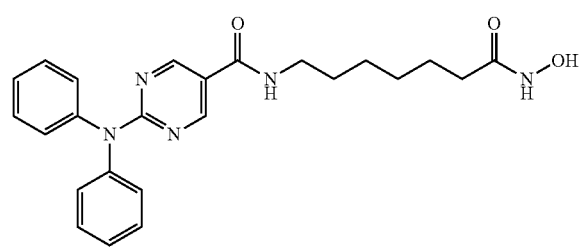 [SMILES: O=C(CCCCCCNC(=O)c1cnc(N(c2ccccc2)c2ccccc2)nc1)NO]

Reaction Scheme

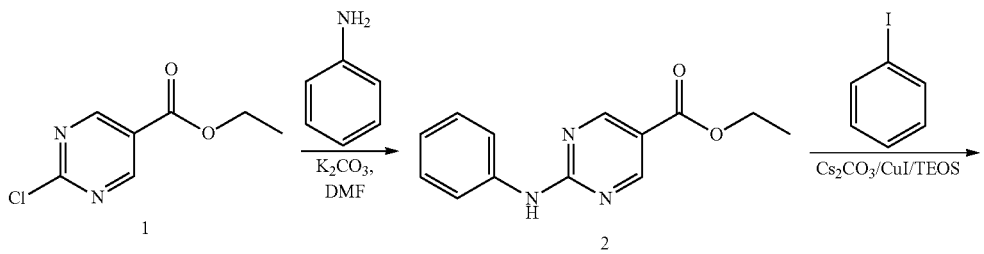

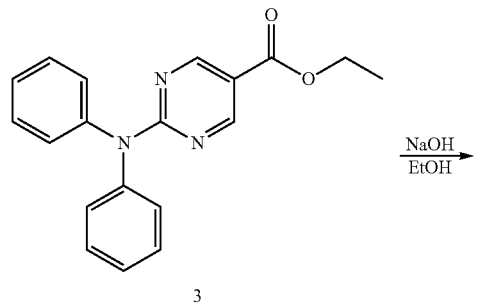

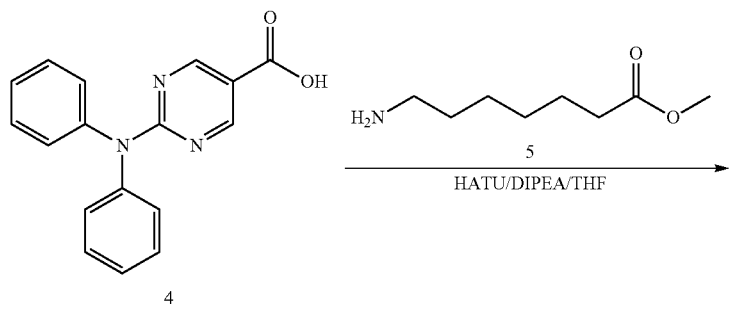

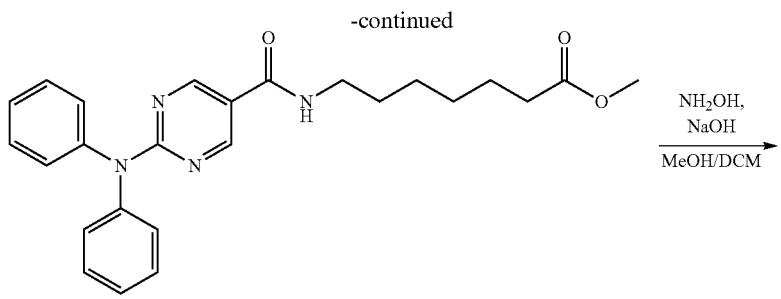

6

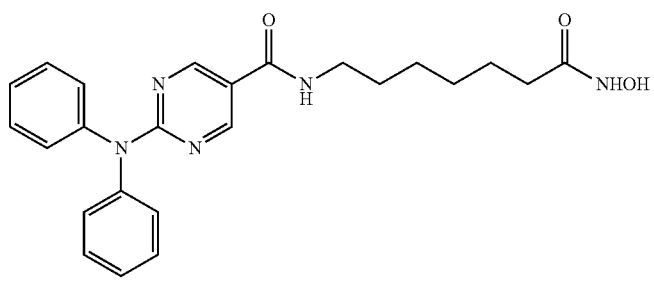

Synthesis of Intermediate 2

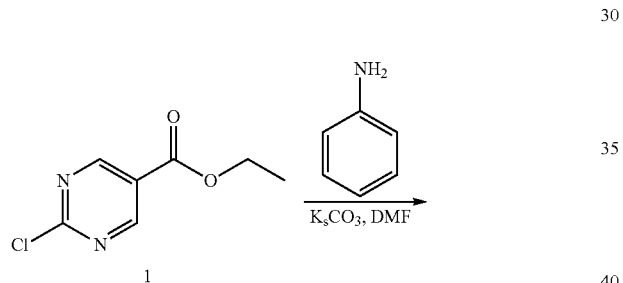

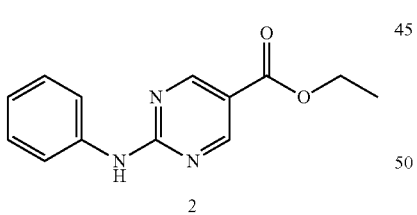

2

A mixture of aniline (3.7 g, 40 mmol), ethyl 2-chloropyrimidine-5-carboxylate 1 (7.5 g, 40 mmol), K$_2$CO$_3$ (11 g, 80 mmol) in DMF (100 ml) was degassed and stirred at 120° C. under N$_2$ overnight. The reaction mixture was cooled to rt and diluted with EtOAc (200 ml), then washed with saturated brine (200 ml×3). The organic layer was separated and dried over Na$_2$SO$_4$, evaporated to dryness and purified by silica gel chromatography (petroleum ethers/EtOAc=10/1) to give the desired product as a white solid (6.2 g, 64%).

Synthesis of Intermediate 3

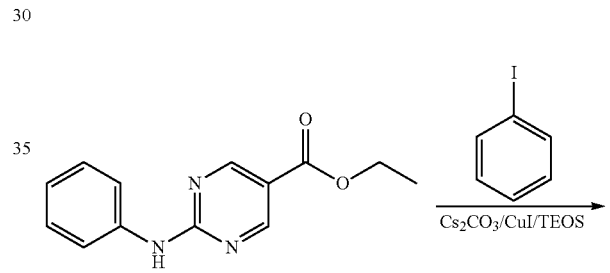

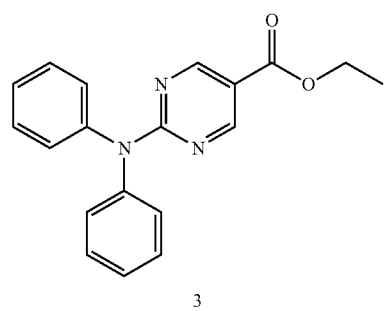

3

A mixture of the compound 2 (6.2 g, 25 mmol), iodobenzene (6.12 g, 30 mmol), CuI (955 mg, 5.0 mmol), Cs$_2$CO$_3$ (16.3 g, 50 mmol) in TEOS (200 ml) was degassed and purged with nitrogen. The resulting mixture was stirred at 140° C. for 14 h. After cooling to rt, the residue was diluted with EtOAc (200 ml) and 95% EtOH (200 ml), NH$_4$F—H$_2$O on silica gel [50 g, pre-prepared by the addition of NH$_4$F (100 g) in water (1500 ml) to silica gel (500 g, 100-200 mesh)] was added, and the resulting mixture was kept at rt for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

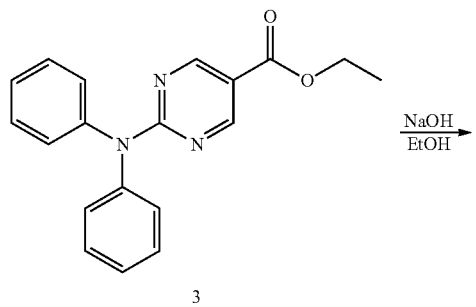

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

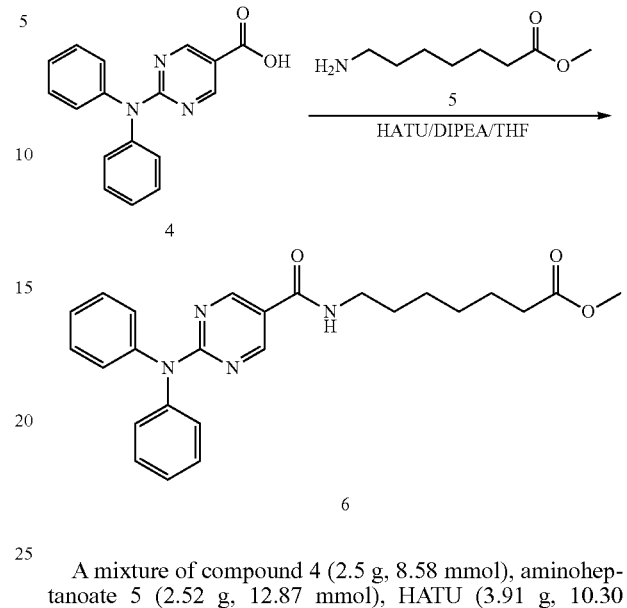

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at rt overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide

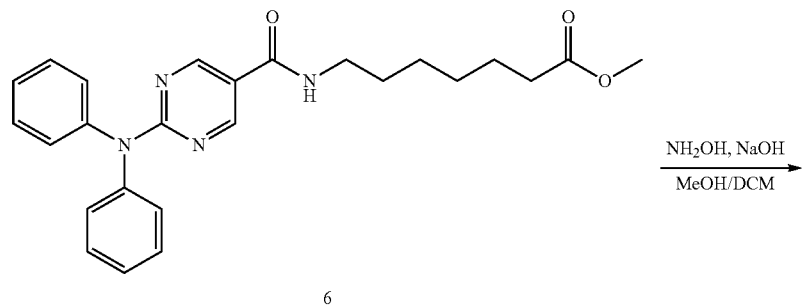

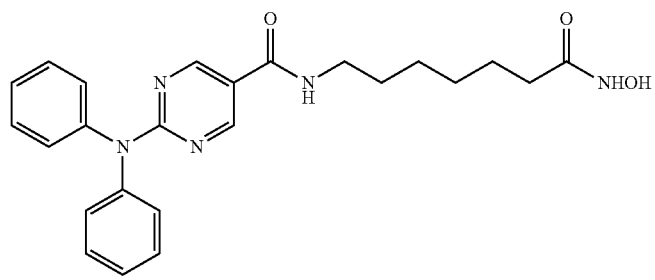

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at rt for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-((2-chlorophenyl)(phenyl)amino)-N-(7-(hydroxyamino)-7-oxoheptyl)pyrimidine-5-carboxamide (Compound B)

Reaction Scheme:

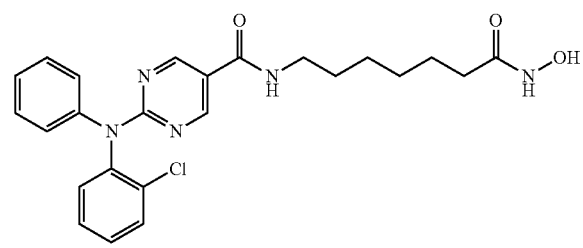 [SMILES: O=C(CCCCCCNC(=O)c1cnc(N(c2ccccc2)c2ccccc2Cl)nc1)NO]

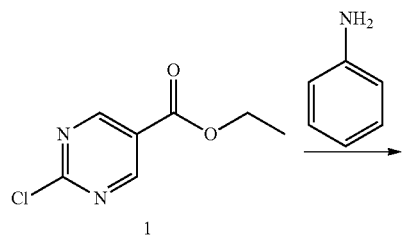

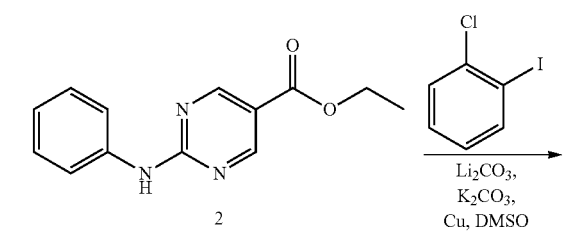

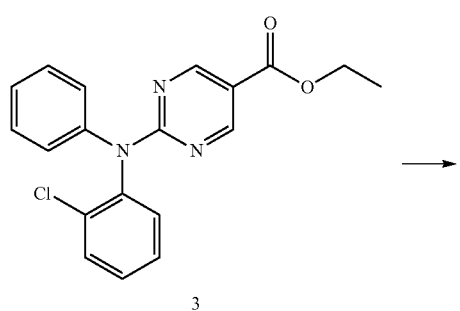

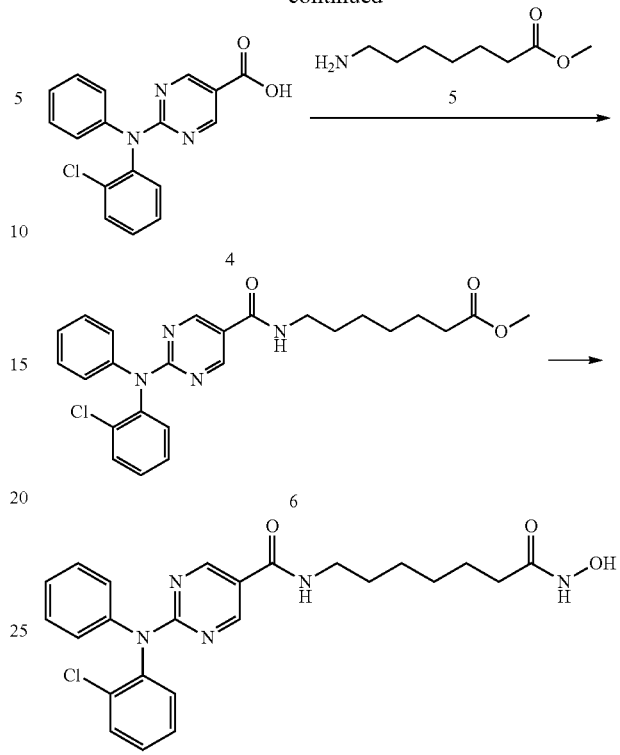

Synthesis of Intermediate 2

See synthesis of intermediate 2 in Example 1.

Synthesis of Intermediate 3

A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4

See synthesis of intermediate 4 in Example 1.

Synthesis of Intermediate 6

See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B)

See synthesis of Compound A in Example 1.

Example 3: Synthesis of 2-((1-(3-fluorophenyl)cyclohexyl)amino)-N-hydroxypyrimidine-5-carboxamide (Compound C)

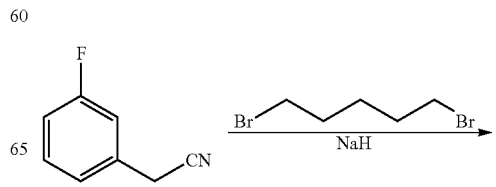

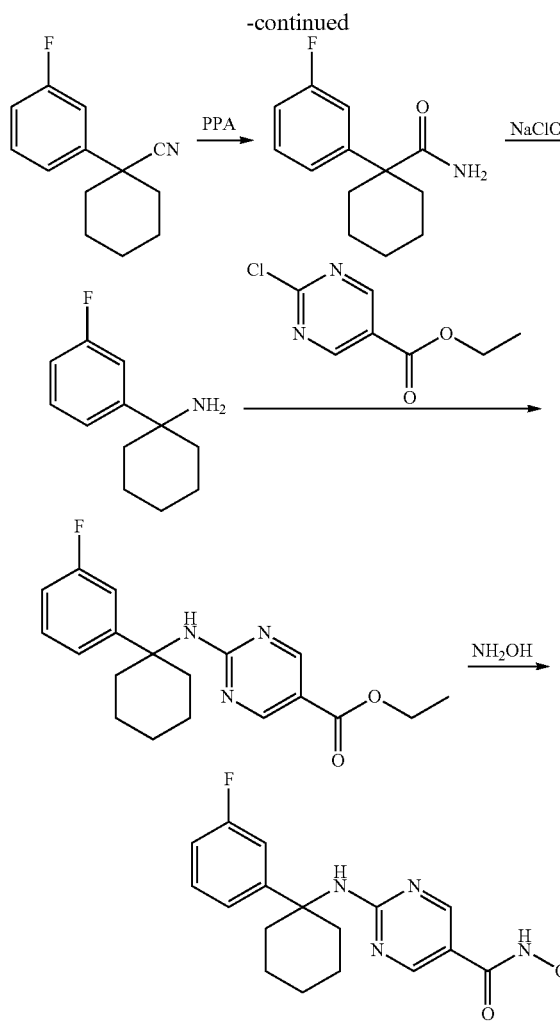

Synthesis of 1-(3-fluorophenyl)cyclohexanecarbonitrile

To a solution of 2-(3-fluorophenyl)acetonitrile (100 g, 0.74 mol) in Dry DMF (1000 ml) was added 1,5-dibromopentane (170 g, 0.74 mol), NaH (65 g, 2.2 eq) was added dropwise at ice bath. After addition, the resulting mixture was vigorously stirred overnight at 50° C. The suspension was quenched by ice water carefully, extracted with ethyl acetate (3*500 ml). The combined organic solution was concentrate to afford the crude which was purified on flash column to give 1-(3-fluorophenyl)cyclohexanecarbonitrile as pale solid (100 g, 67%).

Synthesis of 1-(3-fluorophenyl)cyclohexanecarboxamide

To a solution of 1-(3-fluorophenyl)cyclohexanecarbonitrile (100 g, 0.49 mol) in PPA (500 ml) was heated at 110° C. for about 5-6 hours. After completed, the resulting mixture was carefully basified with sat.NaHCO3 solution until the PH=8-9. The precipitate was collected and washed with water (1000 ml) to afford 1-(3-fluorophenyl)cyclohexanecarboxamide as white solid (95 g, 87%).

Synthesis of 1-(3-fluorophenyl)cyclohexanamine

To a solution of 1-(3-fluorophenyl)cyclohexanecarboxamide (95 g, 0.43 mol) in n-BuOH (800 ml) was added NaClO (260 ml, 1.4 eq), then 3N NaOH (400 ml, 2.8 eq) was added at 0° C. and the reaction was stirred overnight at r.t. The resulting mixture was extracted with EA (2*500 ml), the combined organic solution was washed with brine, dried to afford the crude which was further purification on treating with HCl salt as white powder (72 g, 73%).

Synthesis of ethyl 2-(1-(3-fluorophenyl)cyclohexylamino)pyrimidine-5-carboxylate To a solution of 1-(3-fluorophenyl)cyclohexanamine hydrochloride (2.29 g 10 mmol) in Dioxane (50 ml) was added ethyl 2-chloropyrimidine-5-carboxylate (1.87 g, 1.0 eq) and DIPEA (2.58 g, 2.0 eq). The mixture was heated overnight at 110-120° C. The resulting mixture was directly purified on silica gel column to afford the coupled product as white solid (1.37 g, 40%)

Synthesis of 2-((1-(3-fluorophenyl)cyclohexyl)amino)-N-hydroxypyrimidine-5-carboxamide To a solution of ethyl 2-(1-(3-fluorophenyl)cyclohexylamino)pyrimidine-5-carboxylate (100 mg, 0.29 mmol) in MeOH/DCM (10 ml, 1:1) was added 50% NH2OH in water (2 ml, excess), then sat. NaOH in MeOH (2 ml, excess) was added at 0° C. and the reaction was stirred for 3-4 hours. After completed, the resulting mixture was concentrated and acidified with 2N HCl to the PH=4-5. The precipitate was collected and washed by water (10 ml) to remove the NH2OH and dried to afford 2-((1-(3-fluorophenyl)cyclohexyl)amino)-N-hydroxypyrimidine-5-carboxamide as white powder (70 mg, 73%).

Example 4: Synthesis of N-hydroxy-2-((1-phenylcyclopropyl)amino)pyrimidine-5-carboxamide (Compound D)

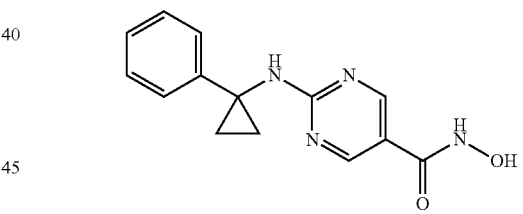

Reaction Scheme

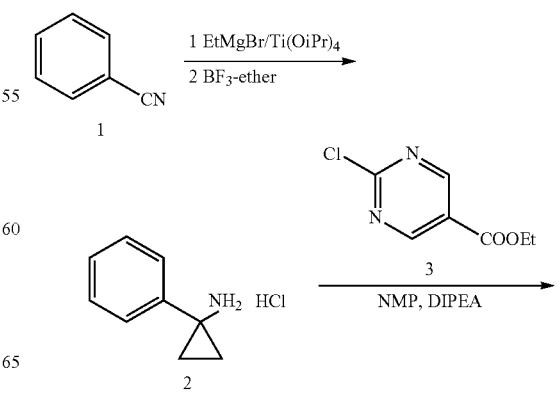

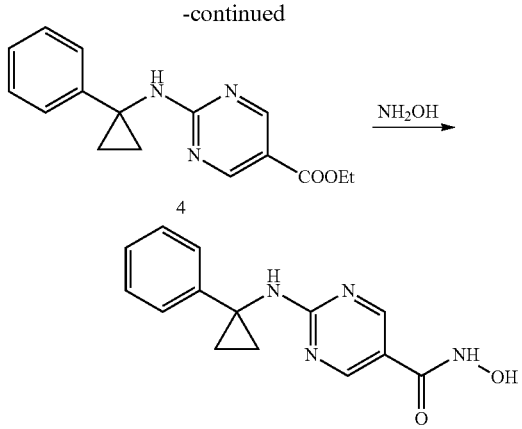

Synthesis of Intermediate 2

A solution of compound 1, benzonitrile, (250 g, 1.0 equiv.), and Ti(OiPr)$_4$ (1330 ml, 1.5 equiv.) in MBTE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4

Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl) amino)pyrimidine-5-carboxamide (Compound D)

A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 μM TCEP) to 6 fold their final concentration. The HDAC enzymes (purchased from BPS Biosciences) were diluted to 1.5 fold their final concentration in assay buffer. The tripeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6). Five μl of compound and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The IC50 was determined using Graph Pad Prism by a four parameter curve fit.

Example 6: HDAC6 Inhibitors Synergize with IMiDs in Lymphoma Cell Killing

In this experiment, it is shown that combining an HDAC6 inhibitor (Compound A, Compound B) with either lenalidomide (Compound E) or pomalidomide (Compound F) leads to synergistic decreases in the viability of the Mino and Jeko1 Mantle Cell Lymphoma (MCL) cells in vitro. The relevance of inhibition of HDAC6 to this synergistic effect was validated by demonstrating synergistic interactions of either IMiD molecule (lenalidomide or pomalidomide) with Compound C, which is more than 300-fold selective for HDAC6 over class I HDAC's.

Briefly, for viability assays, cells were seeded in 384-well plates and treated in quadruplicate in a dose-matrix format with an HDAC6 inhibitor (Compound A, Compound B, or Compound C) in combination with lenalidomide or pomalidomide. After incubating these cells for 72 hr, total cell viability was assessed via an MTS assay (Aqueous One, Promega). The fraction affected (Fa) was subsequently determined for each dose combination and the combination index (CI) was assessed using the method of Chou-Talalay. CI values less than one represent a synergistic effect, values equal to one suggest an additive effect, and values greater than two indicate an antagonistic effect. As can be seen in the Fa-CI plots in FIGS. 1A-F, all HDAC6 inhibitors showed strong evidence of synergy with the tested IMiDs across a broad range of Fa's. This is evidenced by the large number of data points (representing individual dose combinations) in the Fa-CI plot that fall below the highly stringent cutoff of 0.7.

Example 7: HDAC Inhibitors Act Synergistically to Promote Apoptosis in Combination with Immunomodulatory Drugs (IMiDs) in Mantle Cell Lymphoma (MCL) Cells Histone deacetylase (HDAC) inhibitors have demonstrated significant clinical benefit as single agents in cutaneous and peripheral T cell lymphomas, and have received FDA approval for these indications. Ricolinostat (Compound A) is a first-in-class, orally available selective inhibitor of HDAC6 (approximately 11-fold selective over class I HDAC's). Described herein is an assessment of the potential activity of ricolinostat in MCL cell lines in combination with IMiDs.

Figure 2A:
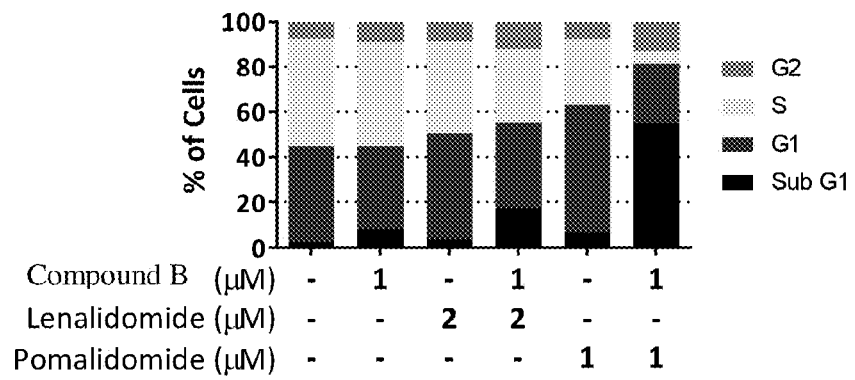
FIG. 2A shows the effect of treatment of Jeko1 mantle cell lymphoma cells for 4 days with DMSO, Compound B (2 µM), Lenalidomide (2 µM), Pomalidomide (1 µM), or combinations of Compound B with either IMiD on cell cycle inhibition. Combination treatment with either IMiD resulted in further reductions in cell cycle progression consistent with decreased proliferation.
Figure 2B:
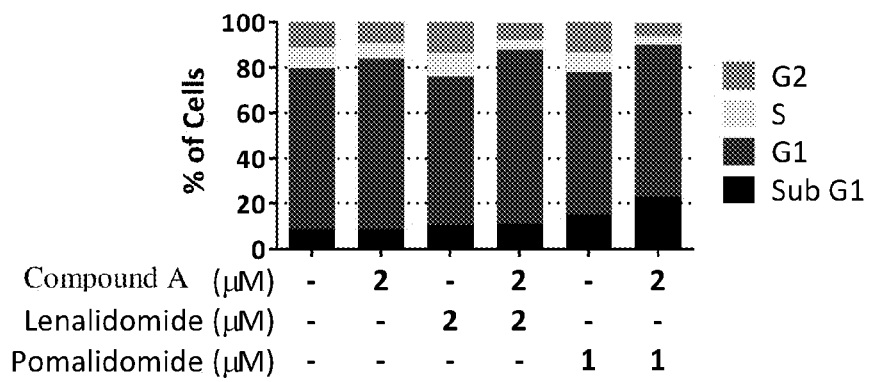
FIG. 2B shows the effect of treatment of Mino mantle cell lymphoma cells for 4 days with DMSO, Compound A (2 µM), Lenalidomide (2 µM), Pomalidomide (1 µM), or combinations of Compound A with either IMiD on cell cycle inhibition. Combination treatment with either IMiD resulted in further reductions in cell cycle progression consistent with decreased proliferation.
Figure 2C:
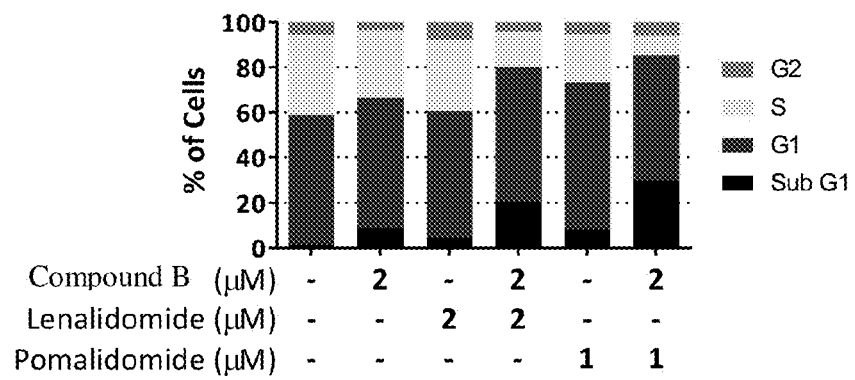
FIG. 2C shows the effect of treatment of Mino mantle cell lymphoma cells for 4 days with DMSO, Compound B (2 µM), Lenalidomide (2 µM), Pomalidomide (1 µM), or combinations of Compound B with either IMiD on cell cycle inhibition. Combination treatment with either IMiD resulted in further reductions in cell cycle progression consistent with decreased proliferation.

FIGS. 2A-C show that treatment of mantle cell lymphoma cells with Compound A or Compound B and/or IMiDs resulted in decreased cell cycle progression. FIG. 2A shows the effect of treatment of Jeko1 mantle cell lymphoma cells for 4 days with DMSO, Compound B (2 μM), Lenalidomide (2 μM), Pomalidomide (1 μM), or combinations of Compound B with either IMiD on cell cycle inhibition. FIG. 2B shows the effect of treatment of Mino mantle cell lymphoma cells for 4 days with DMSO, Compound A (2 μM), Lenalidomide (2 μM), Pomalidomide (1 μM), or combinations of Compound A with either IMiD on cell cycle inhibition. FIG. 2C shows the effect of treatment of Mino mantle cell lymphoma cells for 4 days with DMSO, Compound B (2 μM), Lenalidomide (2 μM), Pomalidomide (1 μM), or combinations of Compound B with either IMiD on cell cycle inhibition.

Figure 3A:
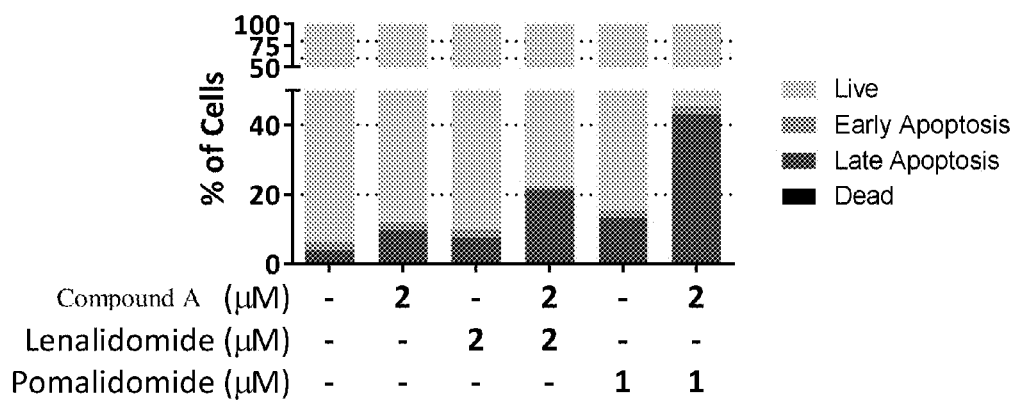
FIG. 3A shows the effect of treatment of Jeko1 mantle cell lymphoma cells for 4 days with DMSO, Compound A (2 µM), Lenalidomide (2 µM), Pomalidomide (1 µM), or combinations of Compound A with either IMiD on the induction of apoptosis. Combination treatment with either IMiD resulted in synergistic increases in cellular apoptosis.
Figure 3B:
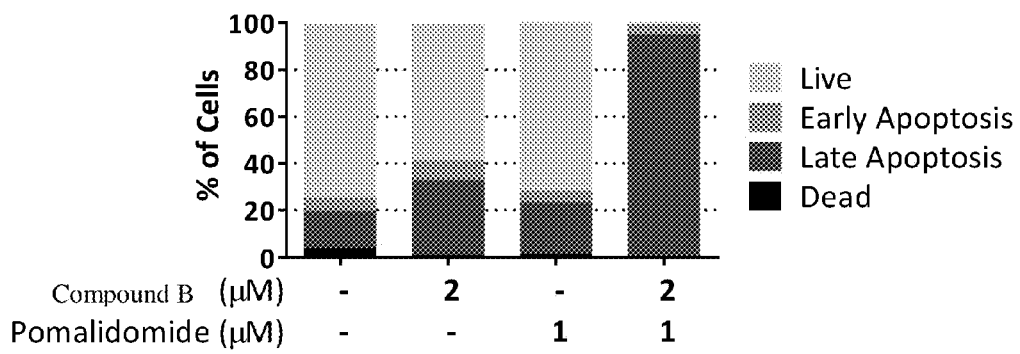
FIG. 3B shows the effect of treatment of Jeko1 mantle cell lymphoma cells for 4 days with DMSO, Compound B (2 µM), Pomalidomide (1 µM), or combinations of Compound B with pomalidomide on the induction of apoptosis. Combination treatment with either IMiD resulted in synergistic increases in cellular apoptosis.

FIGS. 3A-B show that treatment of mantle cell lymphoma cells with Compound A or Compound B and IMiDs resulted in synergistic increases in cellular apoptosis. FIG. 3A shows the effect of treatment of Jeko1 mantle cell lymphoma cells for 4 days with DMSO, Compound A (2 μM), Lenalidomide (2 μM), Pomalidomide (1 μM), or combinations of Compound A with either IMiD on the induction of apoptosis. FIG. 3B shows the effect of treatment of Jeko1 mantle cell lymphoma cells for 4 days with DMSO, Compound B (2 μM), Pomalidomide (1 μM), or combinations of Compound B with pomalidomide on the induction of apoptosis.

Figure 4:
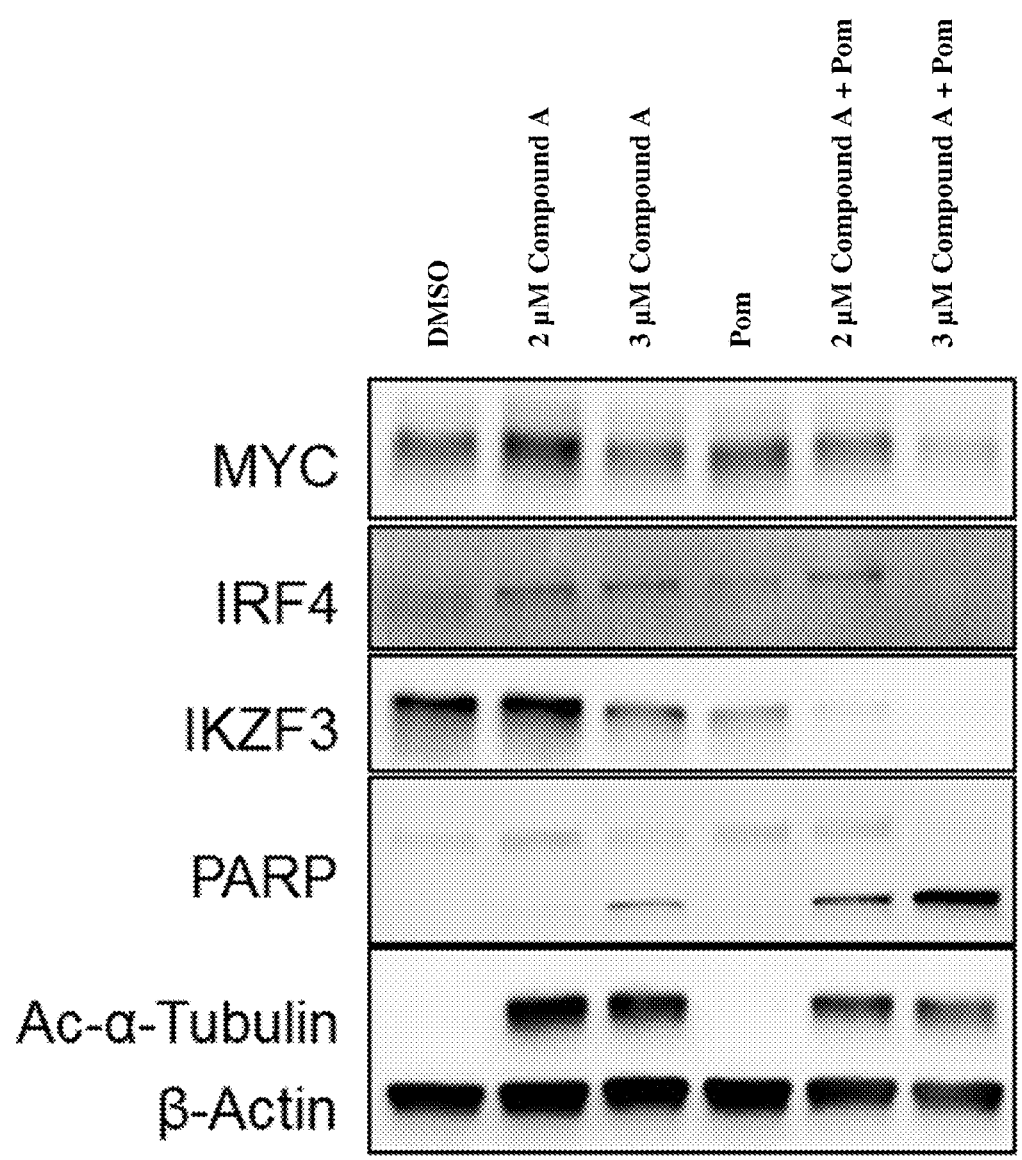
FIG. 4 is a picture of an immunoblot from Jeko1 mantle cell lymphoma cells showing that the combination of Compound A and pomalidomide led to further suppression of MYC, IRF4, and IKZF3 expression, all of which are key transcriptional regulators in cancer. Markers of apoptosis (cleaved PARP) were also increased by combination treatment

FIG. 4 is a picture of an immunoblot from Jeko1 mantle cell lymphoma cells showing that the combination of Compound A and pomalidomide led to further suppression of MYC, IRF4, and IKZF3 expression, all of which are key transcriptional regulators in cancer. Markers of apoptosis (cleaved PARP) were also increased by combination treatment Combination treatment of MCL lines with Compounds A and B and lenalidomide or pomalidomide in a dose-matrix format resulted in synergistic decreases in cell viability in vitro. Reduced cell growth was accompanied by increased apoptosis after combination treatment, as well as reduced expression of the critical oncogenic transcription factors MYC and IRF4. Overall, these data support the continued evaluation of the activity of Compounds A and B in mantle cell lymphoma in combination with either IMiDs.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for treating lymphoma in a subject in need thereof comprising administering to the subject a therapeutically effective amount of a pharmaceutical combination comprising a histone deacetylase 6 (HDAC6) specific inhibitor or a pharmaceutically acceptable salt thereof, and an immunomodulatory drug (IMiD) or a pharmaceutically acceptable salt thereof, wherein the HDAC6 specific inhibitor is

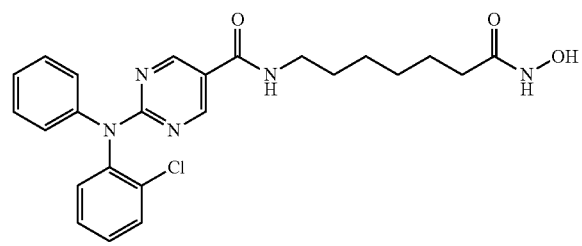 [SMILES: O=C(CCCCCCNC(=O)c1cnc(N(c2ccccc2)c2ccccc2Cl)nc1)NO]

or a pharmaceutically acceptable salt thereof; and wherein the immunomodulatory drug is

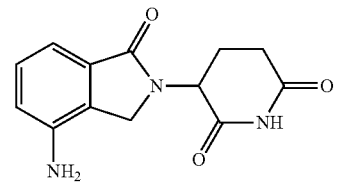 [SMILES: Nc1cccc2c1CN(C1CCC(=O)NC1=O)C2=O]

or a pharmaceutically acceptable salt thereof, or

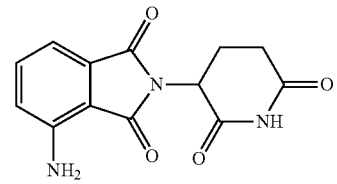 [SMILES: Nc1cccc2c1C(=O)N(C1CCC(=O)NC1=O)C2=O]

or a pharmaceutically acceptable salt thereof.

2. The method of claim 1, wherein the immunomodulatory drug is:

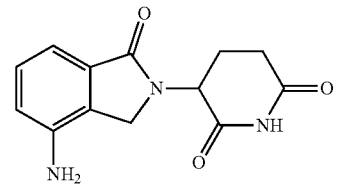 [SMILES: Nc1cccc2c1CN(C1CCC(=O)NC1=O)C2=O]

or a pharmaceutically acceptable salt thereof.

3. The method of claim 1, wherein the subject was previously refractory to a monotherapy comprising the immunomodulatory drug.

4. The method of claim 1, wherein the HDAC inhibitor and the immunomodulatory drug are administered in separate dosage forms.

5. The method of claim 1, wherein the HDAC inhibitor and the immunomodulatory drug are administered in a single dosage form.

6. The method of claim 1, wherein the HDAC inhibitor and the immunomodulatory drug are administered at different times.

7. The method of claim 1, wherein the HDAC inhibitor and the immunomodulatory drug administered at substantially the same time.

* * * * *